(12) United States Patent
Fukuhara et al.

(10) Patent No.: US 8,865,146 B2
(45) Date of Patent: *Oct. 21, 2014

(54) HAIR STYLING METHOD

(75) Inventors: Kazuhisa Fukuhara, Tokyo (JP); Kiyotake Tada, Tokyo (JP); Takashi Kodate, Wakayama (JP); Shuichiro Kobaru, Wakayama (JP)

(73) Assignee: Kao Corporation, Tokyo (JP)

(*) Notice: Subject to any disclaimer, the term of this patent is extended or adjusted under 35 U.S.C. 154(b) by 5 days.

This patent is subject to a terminal disclaimer.

(21) Appl. No.: 13/505,355

(22) PCT Filed: Nov. 18, 2010

(86) PCT No.: PCT/JP2010/070531
§ 371 (c)(1),
(2), (4) Date: May 1, 2012

(87) PCT Pub. No.: WO2011/062210
PCT Pub. Date: May 26, 2011

(65) Prior Publication Data
US 2012/0216823 A1  Aug. 30, 2012

(30) Foreign Application Priority Data
Nov. 18, 2009  (JP) ................ 2009-263402

(51) Int. Cl.
*A61Q 5/06* (2006.01)
*C08G 73/02* (2006.01)
*C08G 81/00* (2006.01)
*A61K 8/898* (2006.01)
*C08G 77/388* (2006.01)
*C08G 77/26* (2006.01)

(52) U.S. Cl.
CPC .............. *A61Q 5/06* (2013.01); *C08G 73/0233* (2013.01); *C08G 81/00* (2013.01); *A61K 8/898* (2013.01); *C08G 77/388* (2013.01); *C08G 77/26* (2013.01)
USPC .................... 424/70.12; 424/70.11

(58) Field of Classification Search
None
See application file for complete search history.

(56) References Cited

U.S. PATENT DOCUMENTS

| | | | |
|---|---|---|---|
| 5,278,269 A | 1/1994 | Mita et al. | |
| 5,747,016 A | 5/1998 | Yui et al. | |
| 2004/0213752 A1 | 10/2004 | Fujinuma et al. | |
| 2005/0063916 A1 | 3/2005 | Ishii et al. | |
| 2006/0045862 A1 | 3/2006 | Tada et al. | |
| 2010/0139681 A1 | 6/2010 | Oshika et al. | |
| 2010/0203002 A1 | 8/2010 | Fukuhara et al. | |
| 2010/0316583 A1 | 12/2010 | Fujinuma et al. | |

FOREIGN PATENT DOCUMENTS

| | | |
|---|---|---|
| CN | 1742701 A | 3/2006 |
| JP | 2 180911 | 7/1990 |
| JP | 3 287509 | 12/1991 |
| JP | 7 133352 | 5/1995 |
| JP | 2004 339216 | 12/2004 |
| JP | 2005 68134 | 3/2005 |
| JP | 2006 69899 | 3/2006 |
| JP | 2009 23963 | 2/2009 |
| JP | 2009 24114 | 2/2009 |
| JP | 2009 149597 | 7/2009 |
| JP | 2009 256367 | 11/2009 |
| JP | 2009-256367 | * 11/2009 |
| JP | 2010 215576 | 9/2010 |
| JP | 2011 63588 | 3/2011 |
| WO | WO 2009/014237 A2 | 1/2009 |
| WO | WO 2009/014237 A3 | 1/2009 |

OTHER PUBLICATIONS

U.S. Appl. No. 13/504,140, filed Apr. 26, 2012, Fukuhara et al.
International Search Report Issued Feb. 22, 2011 in PCT/JP10/70531 Filed Nov. 18, 2010.
Combined Chinese Office Action and Search Report Issued Dec. 4, 2012 in Patent Application No. 201080048468.8 (with English translation and English translation of Categories of Cited Documents).

* cited by examiner

*Primary Examiner* — Jyothsna Venkat
(74) *Attorney, Agent, or Firm* — Oblon, Spivak, McClelland, Maier & Neustadt, L.L.P.

(57) ABSTRACT

A hair styling method, including the steps of:
applying a hair cosmetic composition containing a component (A) to the hair:
Component (A): an organopolysiloxane wherein at least two silicon atoms in organopolysiloxane segments which constitute the main chain of the organopolysiloxane (a) are bound to poly(N-acylalkyleneimine) segments (b) consisting of repeating units represented by the following general formula (1):

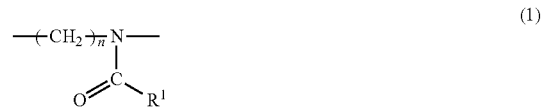

(1)

via respective alkylene groups each containing a hetero atom, wherein the number-average molecular weight of the poly (N-acylalkyleneimine) segments is from 1,200 to 5,500, wherein the mass ratio of the component (a) to the component (b) [i.e., a/b] is from 35/65 to 60/40, wherein the weight-average molecular weights of the organopolysiloxane segments between adjacent two poly(N-acylalkyleneimine) segments (b) are from 1,300 to 5,500, and wherein the weight-average molecular weight of the organopolysiloxane segments (a) is from 7,000 to 100,000;
forming the hair style at a hair temperature of 50° C. or higher;
and subsequently cooling the hair temperature to lower than 50° C. to fix the formed hair style.

10 Claims, No Drawings

HAIR STYLING METHOD

CROSS REFERENCE TO RELATED APPLICATION

This application is a 371 of PCT/JP2010/070531, filed on Nov. 18, 2010, and claims priority to Japanese Patent Application No. 2009-263402, filed on Nov. 18, 2009.

FIELD OF THE INVENTION

The present invention relates to a hair styling method.

BACKGROUND OF THE INVENTION

In order to set a hair style and keep the hair style over a period of time, appropriate hair cosmetic compositions are selected according to a required performance, a desired hair style etc. The hair cosmetic composition, which is used to set a hair style and keep the hair style over a period of time, is roughly classified into the following three types:

1) a hair cosmetic composition for fixing a hair style by effect of a film formed from a film-forming resin,
2) a hair cosmetic composition for fixing a hair style by adhesive force, and
3) a hair cosmetic composition for forming hair style by dissociation and re-formation of hydrogen bonds during the step of permeation of water into the hair and drying the hair.

One example of the hair cosmetic composition of the above 1) for fixing a hair style by effect of a film derived from a film-forming resin is an aerosol type hair cosmetic composition (for example, Patent Document 1). This type of the hair cosmetic composition shows a fixing ability enough to maintain a hair style set once over a whole day. However, the film formed on the surface of hair is firm but brittle, therefore, the there are problems such as, stiffness of the hair; breaking the hair style when external force is applied to the once styled hair and the film is broken; and difficulty in changing the once styled hair (hereinafter, such a changing is hereinafter referred to as "hair restyling"). For this reason, hair styling by using this type of the hair cosmetic composition is carried out by setting a hair style while heating the hair with, for example, a hair drier, and then applying the hair cosmetic composition thereto. When or after this type of the hair cosmetic composition is applied, attention is paid to preventing applying any external force to the styled hair, and further drier is not used. Accordingly, when the hair cosmetic composition is applied, the temperature of the hair is returned to approximately room temperature.

One example of the hair cosmetic composition 2) for fixing a hair style by adhesive force is a hair cosmetic composition wherein a film-forming resin and a plasticizer are used together to provide adhesive force (for example, Patent Documents 2 and 3). This type of the hair cosmetic composition can provide hair restyling ability; however, the hair cosmetic composition involves the problems such as sticking of the hair when the ability for fixing the hair style is increased; while, insufficient ability for fixing hair style when the stickiness is decreased. Further, this type of the hair cosmetic composition can not provide enough force to fix the once styled hair over a whole day.

A hand or a hair styling tool must contact the hair to which the hair cosmetic composition has been applied when restyling the hair. This type of hair cosmetic composition shows a certain ability for fixing hair style based on adhesive force despite they are difference in the degree of the fixing ability, therefore, a certain stickiness is provided onto the hand or tool for hair styling. For this reason, a laborious hair restyling that may cause stickiness, such as hair restyling while heating with a drier, is usually not carried out. Thus, only a slight modification of the hair style is usually made.

Hair styling while heating with a drier is generally selected when styling the hair to which the hair cosmetic compositions of the above type 1) or 2) is not applied.

The hair cosmetic composition 3) is applied to wet or dry hair and the hair is heated with a drier or dried with cool wind, to style the hair. A purpose of this type of the hair cosmetic composition is mainly obtaining smooth combing or brushing ability of the hair. A hair-styling effect of this type of the hair cosmetic composition is considerably weaker than the type 1) or 2) hair cosmetic composition. Some type 3) hair cosmetic compositions supplementally contain a film-forming resin. However, in the case where the amount of the film-forming resin increases, the film formed during the process of drying the hair may become easier to be broken by fingers, a comb, a brush or the like; while in the case where the amount of the film-forming resin decreases, the fixing ability thereof itself is also decreased. In either case, therefore, it would be difficult for the hair cosmetic compositions to provide such a fixing ability that the once styled hair is maintained over a whole day.

Organopolysiloxane is known to be able to provide a number of preferable characteristics, therefore, various forms of the organopolysiloxanes are frequently used for improving feel for touch of shampoos, hair conditioners, and others. For example, a hair setting agent, poly(N-acylalkyleneimine) modified organopolysiloxane, which is not broken or plastically deformed within a predetermined range of elongation rate is disclosed as an example of organopolysiloxane applicable to hair cosmetic compositions for hair styling (Patent Document 4). This organopolysiloxane has advantages as compared with conventional film-forming resins such as a better hair-setting capability, and a better retention performance; a better feel for touch to the styled hair (soft and non-coarse feel); and preferable washability. However, even when this organopolysiloxane-containing hair cosmetic composition is used, fixing ability enough to maintain once styled hair over a whole day cannot be obtained. Moreover, physical property of this organopolysiloxane is hardly changed even when heated; thus, the organopolysiloxane is unsuitable for hair styling with heating.

Further, a poly(N-acylalkyleneimine) modified organopolysiloxane described in Patent Document 5 shows not only preferable elongatability but also preferable solubility or dispersibility in water or lower alcohol. Thus, a hair cosmetic composition containing this polysiloxane can provide a good feel, a flexibility for bearing external force (such as fingers passing through the hair; wind; and vibration), and a natural finish. However, this organopolysiloxane is unsuitable for fixing a styled hair firmly which is due to the preferable elongatability of the siloxane. Moreover, the polysiloxane is generally soft at temperatures from room temperature to 220° C. although physical property of the organopolysiloxane is to some degree changed when heated. Therefore, when hair is styled using such a hair cosmetic composition while heating, inconveniences such as adhering the hair cosmetic composition to the tool are easily occurred. Furthermore, even when the temperature of the hair returns to room temperature, the hair cosmetic composition cannot firmly fix the styled hair thus, the hair cosmetic composition is unsuitable for styling hair while heating.

Patent Document 6 describes a hair cosmetic composition containing a specific branched aliphatic acid or a salt thereof, and the organopolysiloxane described in Patent Document 5.

Additionally, the document describes a hair modifying method using this hair cosmetic composition, the method including applying this hair cosmetic composition to the hair, and then heating the hair. However, the heating is performed simply in order to improve natures of the hair, for example, smoothness of the hair, and continuity of the smoothness. In another word, the heating is not performed in order to arrange the hair style. Actually, the organopolysiloxane described in Patent Document 5 is unsuitable for styling hair while heating as described above.

PRIOR ART DOCUMENTS

Patent Document

Patent Document 1: JP-A-2-180911
Patent Document 2: JP-A-2005-68134
Patent Document 3: JP-A-2009-23963
Patent Document 4: JP-A-07-133352
Patent Document 5: JP-A-2009-24114 (in particular, Example 10 and Comparative Example 2)
Patent Document 6: JP-A-2009-149597 (in particular, Examples 11, 13 and 14)

SUMMARY OF THE INVENTION

The invention provides a hair styling method including the steps of: applying a hair cosmetic composition containing the following component (A) to hair; forming the hair style at a hair temperature of 50° C. or higher; and subsequently cooling the hair temperature to lower than 50° C., thereby fixing the formed hair style.

The component (A) is an organopolysiloxane wherein at least two silicon atoms in organopolysiloxane segments which constitute a main chain of the organopolysiloxane are bound to poly(N-acylalkyleneimine) segments consisting of repeating units represented by the following general formula (1) via alkylene group containing hetero atom:

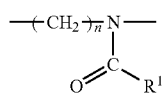

(1)

wherein $R^1$ is a hydrogen atom, an alkyl group having 1 to 22 carbon atoms, an aralkyl group, or an aryl group; and n is 2 or 3, and wherein the number-average molecular weight of the poly (N-acylalkyleneimine) segments is from 1,200 to 5,500, wherein the mass ratio of the organopolysiloxane segments (a) which constitute the main chain to the poly(N-acylalkyleneimine) segments (b) [i.e., a/b] is from 35/65 to 60/40, wherein the weight-average molecular weights of the organopolysiloxane segments of adjacent poly(N-acylalkyleneimine) segments are from 1,300 to 5,500, and wherein the weight-average molecular weight of the organopolysiloxane segments which constitute the main chain is from 7,000 to 100,000.

The invention provides further a hair cosmetic composition containing an organopolysiloxane wherein at least two silicon atoms in organopolysiloxane segments constituting a main chain of the organopolysiloxane are bound to the poly (N-acylalkyleneimine) segments consisting of repeating units represented by the following general formula (1) via alkylene group containing hetero atom:

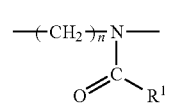

(1)

wherein $R^1$ is a hydrogen atom, an alkyl group having 1 to 22 carbon atoms, an aralkyl group, or an aryl group; and n is 2 or 3, and the number-average molecular weight of the poly(N-acylalkyleneimine) segments is from 1,600 to 3,500, wherein the mass ratio of organopolysiloxane segments (a) which constitute the main chain to the poly(N-acylalkyleneimine) segments (b) [i.e., a/b] is from 42/58 to 58/42, wherein the weight-average molecular weights of the organopolysiloxane segments of adjacent two poly(N-acylalkyleneimine) segments are from 1,600 to 3,500, and wherein the weight-average molecular weight of the organopolysiloxane segments, which constitute the main chain, is from 7,000 to 100,000.

DETAILED DESCRIPTION OF THE INVENTION

The present invention relates to a hair styling method that satisfies whole needs: providing a soft feel and a natural finish to hair, firmly fixing a hair style, keeping the hair style over a long period while bearing external force (such as fingers passing through hair; wind; and vibration), and further restyling the hair; and further relates to a hair cosmetic composition containing an organopolysiloxane that can be preferably used for the above hair styling method.

The inventors have found out that, among organopolysiloxanes having the same structure as the organopolysiloxanes described in Patent Documents 4 to 6, a certain kind of organopolysiloxanes show preferable performances for hair-styling-polymer, for example, giving a soft feel and a natural finish to hair, fixing a style of the hair, and keeping the hair style over a long period and bearing external force (such as fingers passing through hair; wind; and vibration), and show an excellent solubility or dispersibility in water or lower alcohol.

The inventors then have found out that when a hair cosmetic composition containing the above-mentioned organopolysiloxane is used and further used in a specific method of use, the above-mentioned needs can be wholly satisfied, and further the hair cosmetic composition can easily be washed away by hair-washing.

[Hair Styling Method]

The hair styling method of the invention is carried out by applying a hair cosmetic composition containing a component (A) initially to hair, forming hair style at a hair temperature of 50° C. or higher, and then cooling the temperature of the hair to a temperature lower than 50° C. to fix the formed hair style.

—Application of the Hair Cosmetic Composition to Hair

The manner for applying the hair cosmetic composition containing component (A) may be varied according to the type of the form of the hair cosmetic composition, discharging by, for example, spraying, application by hand, a combination thereof, or the like may be used.

Preferably, some water is applied to the hair before the application of the hair cosmetic composition containing component (A) to the hair, because the hair cosmetic composition may fit in the whole hair more easily.

After the hair cosmetic composition containing component (A) is applied to the hair and before the hair style is formed at a hair temperature of 50° C. or higher, the hair is preferably dried since the time necessary for a step of forming the hair style is shortened so that the time necessary for the whole hair styling can be shortened. The way for drying after the application of the hair cosmetic composition may be natural drying, heating or the like.

—Forming Hair Style at Hair Temperature of 50° C. or Higher:

A hair iron, a dryer, a heater, a trowel, a curler, a hot curler, or the like may be used for heating the hair at a temperature of 50° C. or higher. The temperature is preferably from 50 to 220° C., more preferably from 60 to 200° C., even more preferably from 80 to 180° C.

In the invention, the "forming (of hair style)" means shaping the hair style by deformation of the hair. Specific examples thereof include: curling or waving straight hair; straightening curled or waved hair; and modifying the degree of the curling or waving of curled or waved hair. However, the examples of the "forming (of hair style)" do not include setting hair style wherein the hair is merely combed or brushed to restore or arrange a disturbed hair style thereof, since the shape of the hair itself is not changed. Examples of tools used for the "forming (of hair style)" include a hair iron, a comb-attached drier, a trowel, a curler, a hot curler, a comb, and a brush.

In the invention, the timing of the "forming" treatment may be either simultaneous with heating treatment, or not. For example, the treatments may be conducted following the below embodiments:

the hair style is formed with a curler, and subsequently heated with a drier;

the hair style is formed while heating with a drier;

the hair is heated with a drier, and subsequently the hair style is formed with a comb (before the temperature of the hair is not lowered);

the hair is heated substantially simultaneously with forming the hair style with a hair iron; and the hair style is formed while heating with a hot curler. In short, the forming of hair style may be carried out in whatever way, as long as the hair style is formed at a temperature of 50° C. or higher.

The timing of application of the hair cosmetic composition containing component (A) to the hair is not particularly limited, as long as this hair cosmetic composition is applied to the hair during the forming of hair style at a temperature of 50° C. or higher. The timing may be, for example:

the hair style is formed with a curler or the like after the application of the hair cosmetic composition containing component (A), and subsequently the hair is heated (before the hair is released from the curler or the other);

the hair is heated after the hair is styled up with a curler or the like (before the hair is released from the curler or the other), and subsequently the hair cosmetic composition containing component (A) is applied in the state that the hair temperature is 50° C. or higher; and the hair cosmetic composition containing component (A) is applied to the hair after the hair style is formed with a curler or the like (before the hair is released from the curler or the other), and the hair is heated at 50° C. or higher. However, the hair style is preferably formed and heated after the hair cosmetic composition containing component (A) is applied, from the viewpoint of setting the hair style easily and spreading the hair cosmetic composition containing component (A) on hair easily.

—Cooling

In the invention, the wording "cool(ing)" (temperature of hair) means not only lowering the temperature intentionally (by, for example, blowing of cool wind) but also lowering the temperature naturally by effect of the surrounding temperature.

The timing of cooling to a temperature of lower than 50° C. after the hair style is formed may be "before releasing" an action for forming the hair, "simultaneous with the releasing" an action for forming the hair, or "after the releasing" an action for forming the hair. The embodiment of such a cooling may be, for example:

the hair is cooled to a temperature of lower than 50° C. without releasing the action for forming the hair, and subsequently the action for forming the hair (for example, treatment with a curler, or the like) is released;

the hair is cooled to a temperature of lower than 50° C. simultaneously with releasing the action for forming the hair (for example, by releasing the curling using a hair iron set at a temperature of 50° C., the release of the action and the cooling to a temperature lower than 50° C. substantially simultaneously occur); and the hair is cooled to a temperature of lower than 50° C. after the action for forming the hair is released (if the period after the release is too long in this case, the once formed hair style may not be kept; therefore, the hair is preferably cooled just after the release. For example, in the case where the setting of temperature of the hair iron is higher than 50° C., or where hair tress curled on the hair iron are thicker, the period necessary for the hair to be cooled to a temperature of lower than 50° C. after the release of the curling hair tress would be longer. However, such embodiments are also allowable as far as the formed hair style is maintained. Alternatively, the temperature of the hair may be 50° C. or higher in a short time after the release of the action for forming the hair style). The wording "just after" herein means a timing of preferably after 30 seconds or less, more preferably 15 seconds or less, even more preferably 5 seconds or less, even more preferably 3 seconds or less.

Hair Restyling

The organopolysiloxane of the component (A) used for the hair styling method of the subject invention shows a characteristic thermoplasticity in that the organopolysiloxane softens when heated to 50° C. or higher and restores its elasticity immediately after cooling. Therefore, even after the hair is once styled, the hair can easily be restyled repeatedly. For this reason, even when the hair style is once unsuccessfully formed, the hair style can easily be modified. Thus, even if a person who is not accustomed to hair styling can easily make a satisfactory hair style. The hair restyling in this case may be carried out according to: re-forming the hair style once styled according to the hair styling method of the subject invention at a hair temperature of 50° C. or higher; and subsequently forming the hair style while cooling the hair temperature to lower than 50° C. A specific example of the method is same method as described above. During the method, the hair cosmetic composition containing component (A) may be additionally applied to the hair. However, the hair restyling can be carried out without additional application, since the hair cosmetic composition containing component (A) has already been applied thereto during the previous hair styling procedure.

[Component (A): Organopolysiloxane]

The organopolysiloxane of the component (A) used according to the hair styling method of the subject invention is a compound wherein at least two silicon atoms in organopolysiloxane segments which constitute the main chain of the organopolysiloxane are bound to poly(N-acylalkyleneimine) segments which consists of repeating units represented by the general formula (1) via alkylene groups containing heteroatom(s). The thermoplasticity of the organopolysiloxane is characteristic in that, when the organopolysiloxane is heated to the temperature range of 50 to 220° C., within the heat tolerance of hair, the organopolysiloxane softens and the elasticity thereof is immediately recovered while the temperature of the organopolysiloxane is returned to room temperature after the heating is stopped.

At least two poly(N-acylalkyleneimine) segments may be bound to any silicon atoms constituting the organopolysiloxane segments via heteroatom-containing alkylene groups. Preferably, one or more of the silicon atoms, which are not present at both ends (of the organopolysiloxane) are bound to the poly(N-acylalkyleneimine) segments via the above-mentioned alkylene groups. More preferably, two or more of the silicon atoms which are not present at both the ends are bound to the poly(N-acylalkyleneimine) segments via the above-mentioned respective alkylene groups.

The heteroatom-containing alkylene group functions as a liking group for the poly(N-acylalkyleneimine) segments. This alkylene group is, for example, an alkylene group having 2 to 20 carbon atoms and containing 1 to 3 nitrogen, oxygen, or sulfur atoms, and is preferably a group represented by any one of formulae (i) to (viii) illustrated below, more preferably a group represented by any one of the formulae (i) to (iii) illustrated below. In each of the formulae, An$^-$ is a counter ion of a quaternary ammonium salt, and examples thereof include an ethylsulfate ion, a methylsulfate ion, a chloride ion, a iodide ion, a sulfate ion, a p-toluenesulfonate ion, and a perchlorate ion.

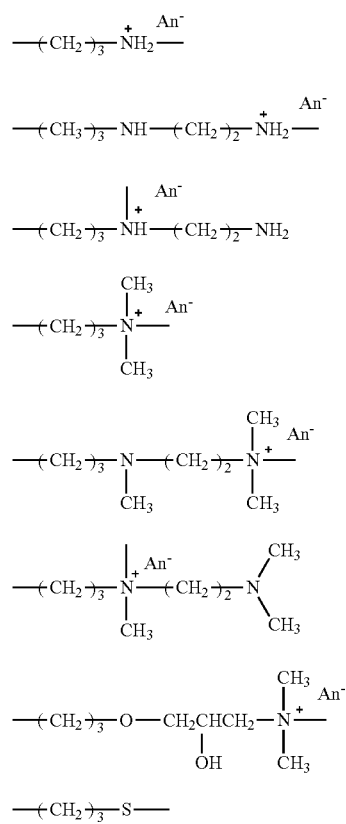

Examples of the alkyl group having 1 to 22 carbon atoms as R$^1$ in the general formula (1) in the N-acylalkyleneimine units constituting the poly(N-acylalkyleneimine) segment include a linear, branched or cyclic alkyl group having 1 to 22 carbon atoms. Specific examples thereof include methyl, ethyl, n-propyl, isopropyl, n-butyl, tert-butyl, pentyl, hexyl, cyclohexyl, heptyl, octyl, nonyl, decyl, undecyl, dodecyl, octadecyl, nonadecyl, eicosyl, and docosyl groups. Of these groups, alkyl group having 1 to 10 carbon atoms is preferred, alkyl group having 1 to 6 carbon atoms is more preferred and alkyl group having 1 to 3 carbon atoms is even more preferred from the viewpoint of preferable solubility in water or lower alcohol.

The examples of the aralkyl group include an aralkyl group having 7 to 15 carbon atoms. Specific examples thereof include benzyl, phenethyl, trityl, naphthylmethyl, and anthracenylmethyl groups. Of these groups, aralkyl group having 7 to 14 carbon atoms is preferred, and aralkyl group having 7 to 10 carbon atoms is more preferred.

The examples of the aryl group include an aryl group having 6 to 14 carbon atoms. Specific examples thereof include phenyl, tolyl, xylyl, naphthyl, biphenyl, anthryl, and phenanthryl groups. Of these groups, aryl group having 6 to 12 carbon atoms is preferred, and aryl group having 6 to 9 carbon atoms is more preferred.

Of these groups, the R$^1$ is preferably alkyl group having 1 to 6 carbon atoms, and alkyl group having 1 to 3 carbon atoms is more preferred.

The mass ratio of the organopolysiloxane segments (a) to the poly(N-acylalkyleneimine) segments (b) [i.e., a/b] is from 35/65 to 60/40. The ratio is preferably from 42/58 to 58/42, more preferably from 45/55 to 55/45, even more preferably from 47/53 to 53/47, from the viewpoint of maintaining preferable balance between preferable solubility or dispersibility of the component (A) into a solvent, preferable hair forming performance during styling of the hair, preferable feel for touch of the hair after the styling, and preferable setting ability for retaining the styled hair over a long period, such a balance being more suitable for the hair styling method of the subject invention.

In the present specification, the mass ratio [a/b] by mass is a value obtained from analyzing the integration ratio between alkyl groups or phenyl groups in the organopolysiloxane segments and methylene groups in the poly(N-acylalkyleneimine) segments by nuclear magnetic resonance ($^1$H-NMR) after dissolving the organopolysiloxane in the subject invention to deuterium chloroform to provide a solution of 5% concentration by mass.

The weight-average molecular weight (MWg) of the organopolysiloxane segments between adjacent poly(N-acylalkyleneimine) segments (the MWg may be hereinafter referred to as "molecular weight between the graft points") is from 1300 to 5500, preferably from 1600 to 3500, more preferably from 1800 to 3200, even more preferably from 2,000 to 3,000.

In the specification, as represented by a formula (2) illustrated below, the "organopolysiloxane segments between adjacent poly(N-acylalkyleneimine) segments" is a moiety which is surrounded by a broken line between two points, from a binding point where the poly(N-acylalkyleneimine) segment is bound to the organopolysiloxane segment (binding point α) to a binding point where the adjacent poly(N-acylalkyleneimine) segment is bound to this organopolysiloxane segment (binding point β), which is a segment composed of a single R$^2$SiO unit, a single R$^6$, and (y+1)-number of (R$^2$)$_2$SiO units. The "poly(N-acylalkyleneimine) segments" is —W—R$^7$ binding to the R$^6$.

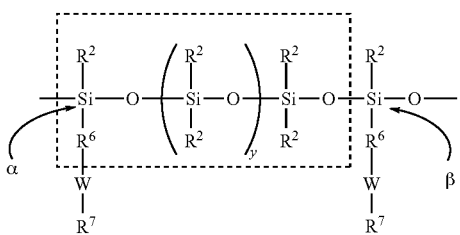

(2)

In the general formula (2), $R^2$ is independently an alkyl group having 1 to 22 carbon atoms, or a phenyl group; $R^6$ is an alkylene group containing heteroatom; —W—$R^7$ is a poly(N-acylalkyleneimine) segment; $R^7$ is a residue of a polymerization initiator; and y is a positive number.

The molecular weight between the graft points (MWg) is the molecular weight of the moiety surrounded by the broken line in the general formula (2), which may correspond to the mass of the organopolysiloxane segments per mole of the poly(N-acylalkyleneimine) segments (g/mol). When functional groups of a modified organopolysiloxane that is a starting compound are wholly substituted with the poly(N-acylalkyleneimine), the molecular weights between the graft points are consistent with the functional equivalent (g/mol) of the modified organopolysiloxane.

The molecular weight ($MW_{ox}$) of the poly(N-acylalkyleneimine) segments is calculated from the molecular weight and the polymerization degree of N-acylalkyleneimine units thereof, or may be calculated by a gel permeation chromatography (GPC) measuring method described later. In the subject invention, the molecular weight ($MW_{ox}$) shall mean the number-average molecular weight measured by the gel permeation chromatography (GPC) measuring method. The $MW_{ox}$ of the component (A) is from 1,200 to 5,500, preferably from 1,600 to 3,500, more preferably from 1,800 to 3,200, even more preferably from 2,000 to 3,000. According to these molecular weight ranges, the hair cosmetic composition is sufficiently softened at 50° C. or higher to be a state suitable for forming hair style. Furthermore, at a temperature lower than 50° C., preferably at room temperature, the hair cosmetic composition provides both firmness sufficient for keeping the hair style and preferable feel for touch.

The molecular weight MWg between the graft points can be calculated according to the following equation (I), using the content ratio of the organopolysiloxane segment constituting main-chain (Csi):

$$MWg = \frac{Csi \times MWox}{100 - Csi} \quad (I)$$

The weight-average molecular weight (MWsi) of the organopolysiloxane segment constituting main-chain is from 7,000 to 100,000, preferably from 10,000 to 80,000, more preferably from 20,000 to 60,000, even more preferably from 30,000 to 50,000, from the viewpoint of the solubility (of the organopolysiloxane) in a polar solvent such as water, and the handleability of the dissolved organopolysiloxane. The MWsi is substantially equal to the weight-average molecular weight of the modified organopolysiloxane, which is the starting compound, since these compounds have a common structure. The average molecular weight of the modified organopolysiloxane, which is the starting compound, is measured by GPC under conditions described below, and then converted into a molecular weight as a standard polystyrene equivalent.

Column: Super HZ4000+Super HZ2000 (manufactured by Tosoh Corp.)
Eluent: 1 mM triethylamine in THF
Flow rate: 0.35 mL/min.
Column temperature: 40° C.
Detector: UV
Sample: 50 μL The weight-average molecular weight (MWt) of the organopolysiloxane of the component (A) is preferably from 7000 to 100000, more preferably from 20000 to 60000, even more preferably from 30000 to 50000, from the viewpoint that the organopolysiloxane can provide preferable feel to hair, and solubility thereof in a polar solvent such as water can be improved. Furthermore, the hair cosmetic composition involving both setting-performance and set-retaining performance can be provided accordingly. In the subject invention, the MWt can be calculated from the weight-average molecular weight of the modified organopolysiloxane as the starting compound and the above-mentioned mass ratio [a/b].

A process for producing the organopolysiloxane in the subject invention is described below.

The organopolysiloxane in the subject invention may be produced, for example, by reaction between a modified organopolysiloxane represented by the following general formula (3):

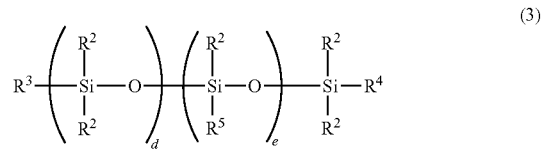

(3)

wherein $R^2$ is the same as described above; and $R^3$ and $R^4$ are each a group identical to $R^2$, or a monovalent group represented by any one of the following formulae (ix) to (xiv):

(ix)

(x)

(xi)

(xii)

(xiii)

(xiv)

$R^5$ is a monovalent group represented by any one of the formulae (ix) to (xiv); d is an integer of 89 to 1332; e is an integer of 2 to 77, and a terminal-reactive poly(N-acylalkyleneimine) yielded by ring-opening-polymerization of a cyclic imino ether represented by the following general formula (4):

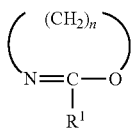

(4)

wherein $R^1$ and n are the same as described above (hereinafter the ether is referred to as "cyclic imino ether (4)").

The modified organopolysiloxane (3) used in the subject invention is a modified organopolysiloxane having a functional equivalent ranging from 1,700 to 3,500, more preferably from 1,800 to 3,200, even more preferably from 2,000 to 3,000, and a weight-average molecular weight ranging preferably from 7,000 to 100,000, more preferably from 10,000 to 80,000, even more preferably from 30,000 to 50,000. The weight-average molecular weight of the modified organopolysiloxane (3), as a raw material, is substantially equal to the weight-average molecular weight (MWsi) of the organopolysiloxane segment constituting main-chain.

The molecular weight of the terminal-reactive poly(N-acylalkyleneimine) is preferably adjusted to fall within the range preferably from 1,200 to 5,500, preferably from 1,600 to 3,500, more preferably from 1,800 to 3,200, even more preferably from 2,000 to 3,000. This is substantially equal to the molecular weight ($MW_{OX}$) of the above-mentioned poly(N-acylalkyleneimine) segments.

Polymerization initiator may be used for the ring-opening polymerization of the cyclic imino ether (4). The polymerization initiator may be a compound having potent electrophilic reactivity, for example, an alkyl ester of a strong acid such as an alkyl benzenesulfonate, an alkyl p-toluenesulfonate, an alkyl trifluoromethanesulfonate, an alkyl trifluoroacetate, and a dialkyl sulfate. Among these, a dialkyl sulfate is preferably used. The amount of the polymerization initiator for use is usually 1 mole for 2 to 100 moles of the cyclic imino ether (4).

A polymerization solvent may be, for example, an acetate such as ethyl acetate or propyl acetate, an ether such as diethyl ether, diisopropyl ether, dioxane and tetrahydrofuran, a ketone such as acetone or methyl ethyl ketone, a halogen solvent such as chloroform and methylene chloride, a nitrile solvent such as acetonitrile and benzonitrile, or an aprotic polar solvent such as N,N-dimethylformamide, N,N-dimethylacetamide, and dimethylsulfoxide. Among these, acetate is preferably used. The amount of the solvent for use is usually from 20 to 2,000 parts by mass to 100 parts by mass of the cyclic imino ether (4).

The polymerization temperature is usually from 30 to 170° C., preferably from 40 to 150° C., and the time for polymerization, which may be varied according to the polymerization temperature or the like, is usually from 1 to 60 hours.

When, for example, 2-substituted-2-oxazoline is used as the cyclic imino ether (4), poly(N-acylethyleneimine), wherein n is 2 in the general formula (1), is yielded. When, for example, 2-substituted-dihydro-2-oxazine is used as the cyclic imino ether (4), poly(N-acylpropyleneimine), wherein n is 3 in the general formula (1), is yielded.

Examples of the method for connecting between the poly (N-acylalkyleneimine) and the organopolysiloxane segment include the following methods:

1) A method by reaction between the terminal-reactive poly(N-acylalkyleneimine), which is yielded by living-polymerizing the cyclic imino ether, and the modified organopolysiloxane represented by the general formula (3), 2) an ester-producing reaction based on condensation between carboxyl groups and hydroxyl groups, 3) an amide-producing reaction based on condensation between carboxyl groups and amino groups, 4) a secondary-, tertiary-, or quaternary-ammonium-producing reaction between halogenated alkyl groups and primary, secondary or tertiary amino groups, 5) an addition reaction of an organopolysiloxane having Si—H group to vinyl groups, and 6) a β-hydroxyamine-producing reaction between epoxy groups and amino groups.

Among them, the method 1) is the most effective method, because the polymerization degree can be controlled easily by the amounts of use of the cyclic imino ether 4) and the polymerization initiator using the following theoretical equation (II), and further substantially monodispersive poly(N-acylalkyleneimine) having a narrower molecular weight distribution than that of obtained from ordinary radical polymerization method:

MWi=(Mole Number of Cyclic Imino Ether)/(Mole Number of Polymerization Initiator)×Molecular Weight of Cyclic Imino Ether+Molecular Weight of Polymerization Initiator (II)

wherein MWi: the molecular weight of the poly(N-acylalkyleneimine).

The organopolysiloxane of the component (A) has a specific structure, wherein poly(N-acylalkyleneimine) segments are bound, respectively, to at least two silicon atoms of organopolysiloxane segments having a predetermined molecular weight via alkylene group containing heteroatom, and wherein the imine segments are arranged at predetermined intervals and are contained in a predetermined proportion. As a result, the hair cosmetic composition having physical properties suitable for use in the hair styling method of the subject invention, characterized in that the hair cosmetic composition is appropriately softened at 50° C. or higher, setting ability for retaining the hair style is maintained over a long period at a temperature lower than 50° C. (preferably around room temperature), preferable feel for touch is maintained and natural finish which is stable even when external force is applied thereto, can be prepared. Additionally, the organopolysiloxane can be dissolved in a polar solvent such as water or lower alcohol.

Preferred examples of the organopolysiloxane of the component (A) include poly(N-formylethyleneimine)organosiloxane, poly(N-acetylethyleneimine)organosiloxane, and poly(N-propionylethyleneimine)organosiloxane.

[Hair Cosmetic Composition]

The hair cosmetic composition used in the subject invention contains the above-mentioned organopolysiloxane of the component (A). Accordingly, the hair cosmetic composition provides soft feel for touch; hair setting performance which is stable even when fingers are passed through the hair; and more natural finish.

The organopolysiloxane of the component (A) may be used alone or may be in combination of two or more thereof. The amount thereof is preferably from 0.01 to 50% by mass, more preferably from 0.05 to 30% by mass, even more preferably from 0.1 to 20% by mass, even more preferably from 0.5 to 10% by mass of the whole of the hair cosmetic composition, from the viewpoint of preferable hair setting performance, preferable retaining performance of the setting, and preferable washability during hair washing. When the amount is adjusted within this range, in the case of using an organic solvent described below and an organic acid or a salt thereof together, both setting-performance and set-retaining performance are improved without decreasing hair-modifying effects (such as improvement of manageability of hair) derived from the organic acid and the organic solvent.

The hair cosmetic composition of the invention may optionally contain, as a preferred component, an organic solvent selected from the following (b1) to (b5) (hereinafter, the solvent is referred to as the "component (B)").

(b1) a compound represented by the following general formula (5):

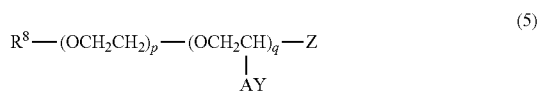

wherein $R^8$ is a hydrogen atom, an alkyl group having 1 to 6 carbon atoms, or a group of $R^9$ wherein $R^9$ is a hydrogen atom, or a methyl or methoxy group, $R^{10}$ is a linking bond, or a saturated or unsaturated bivalent hydrocarbon group having 1 to 3 carbon atoms, and Ph is a para-phenylene group; A is a linking bond, or a saturated bivalent hydrocarbon group having 1 to 4 carbon atoms; Y and Z are independently a hydrogen atom or a hydroxyl group; and p and q each independently are an integer of 0 to 5, provided that when p and q are each zero, Z is a hydroxyl group and $R^8$ is neither a hydrogen atom, an alkyl group having 1 to 3 carbon atoms nor a group of —$R^9$-Ph;

(b2) an N-alkylpyrrolidone or N-alkenylpyrrolidone having a nitrogen atom to which an alkyl or alkenyl group having 1 to 18 carbon atoms is bound;

(b3) an alkylene carbonate having 2 to 4 carbon atoms;

(b4) polypropylene glycol having a number-average molecular weight of 100 to 1,000; and (b5) a lactone or cyclic ketone represented by the following general formula (6), (7) or (8):

wherein X is a methylene group or an oxygen atom; $R^{11}$ and $R^{12}$ are substituents different from each other; and a and b each independently are 0 or 1.

Examples of the compound (b1) of the organic solvents of the component (B) include aliphatic linear or branched C4 to C6 alcohols such as butanol and isobutanol, ethylene glycol, propylene glycol, dipropylene glycol, 1,3-butanediol, benzyl alcohol, cinnamyl alcohol, phenethyl alcohol, p-anisyl alcohol, p-methylbenzyl alcohol, phenoxyethanol, 2-benzyloxyethanol, methyl carbitol, ethyl carbitol, propyl carbitol, butyl carbitol, triethylene glycol monoethyl ether, and triethylene glycol monobutyl ether.

Examples of the compound (b2) include N-methylpyrrolidone, N-octylpyrrolidone, and N-laurylpyrrolidone.

Examples of the compound (b3) include ethylene carbonate, and propylene carbonate.

The polypropylene glycol (b4), which has a number-average molecular weight of 100 to 1,000, is preferably a polypropylene glycol having a number-average molecular weight of 300 to 500. The number-average molecular weight referred to herein is a number-average molecular weight in terms of polystyrene that is measured by GPC.

In the compound (b5), $R^{11}$ and $R^{12}$ in the general formulae (6) to (8) are preferably a linear, branched or cyclic alkyl, hydroxyl, sulfonate, phosphate, carboxy, phenyl, sulfoalkyl, alkyl phosphate or carboxyalkyl group, or the like. Among these, preferred is a linear or branched alkyl group having 1 to 6 carbon atoms, such as a methyl, ethyl, propyl, isopropyl or butyl group. When the compound (b5) is a γ-lactone, these groups are preferably bound, as a substituent, to the γ-position. When the compound (b5) is a δ-lactone, these groups are preferably bound, as a substituent, to the δ-position (that is, methylene adjacent to the oxygen heteroatom). When it is desired to increase the water solubility of each of the compounds (6) to (8), it is preferred that the compound has, as $R^{11}$ or $R^{12}$, an acidic group such as a sulfonate, phosphate or carboxyl group, or an alkyl group substituted with one or more of these groups. Examples of the compound (b5) as the lactone include γ-butyrolactone, γ-caprolactone, γ-valerolactone, δ-valerolactone, δ-caprolactone, and δ-heptanolactone. From the viewpoint of the stability of the lactone, γ-lactone is preferred, γ-butyrolactone or γ-caprolactone is more preferred. Examples of the compound (b5) as the cyclic ketone include cyclopentanone, cyclohexanone, cycloheptanone, and 4-methylcycloheptanone.

The component (B) used in the invention is preferably in a liquid format 25° C., and further preferably has a C log P of −2 to 3. The C log P is more preferably from −1 to 2, from the viewpoint of the promotion of penetration of the hair cosmetic composition. The C log P (of a substance) is a calculated value of an octanol/water distribution coefficient (log P), which is an index representing the distribution of the substance between an octanol phase and an aqueous phase, and is defined by the following equation (III) (examples thereof are described in Chemical Review, Vol. 71, No. 6 (1971)):

$$\log P = \log([\text{substance}]_{Octanol}/[\text{substance}]_{Water}) \quad (III)$$

wherein [substance]$_{Octanol}$ represents the molar concentration of the substance in the phase of 1-octanol; and [substance]$_{Water}$ represents the molar concentration of the substance in the aqueous phase.

The C log P values of major examples of the component (B) are as follows: dipropylene glycol (−0.67), 1,3-butanediol (−0.29), benzyl alcohol (1.1), 2-benzyloxyethanol (1.2), 2-phenylethanol (1.2), 1-phenoxy-2-propanol (1.1), polypropylene glycol 400 (0.9), propylene carbonate (−0.41), and γ-butyrolactone (−0.64). Of these components (B), benzyl alcohol and 2-benzyloxyethanol are preferred.

Two or more species of the component (B) may be used in combination. The total content thereof in the hair cosmetic composition is preferably from 0.1 to 40% by mass, more preferably from 0.5 to 10% by mass, even more preferably from 1 to 5% by mass, from the viewpoint of promotion of effect for improving bounce and resilience of hair after the hair is washed, effect for improving hair-softness and hair-manageability, and modifying effects (such as an improvement of elasticity of hair and moisture resistance), and from the viewpoint that the component (B) can be compatible with the component (A) to improve the hair setting performance of the hair cosmetic composition.

The hair cosmetic composition used in the subject invention may contain, as a solvent, water, or any linear or branched saturated or unsaturated C1 to C3 alcohol, from the viewpoint of improvement of hair-setting-performance, feel for use and solubility during preparation of the hair cosmetic composition. These solvents may be used alone or in combination of two or more. Of these solvents, water, ethanol, and isopropanol are preferred, and water and ethanol are more preferred. The total content of water and the linear or branched saturated or unsaturated C1 to C3 alcohol is preferably from 0.1 to 98% by mass, more preferably from 1 to 90% by mass, even more preferably from 5 to 60% by mass of the whole of the hair cosmetic composition.

The hair cosmetic composition used in the subject invention may contain, besides the component (B), an organic carboxylic acid which may have a hydroxyl group, or a salt thereof (hereinafter referred to as the component (C)). In this case, more preferred examples of the component (B) include dipropylene glycol, 1,3-butanediol, benzyl alcohol, phenoxyethanol, 2-benzyloxyethanol, propylene carbonate, and polypropylene glycol (number-average molecular weight: 300 to 500, more preferably 400).

The organic carboxylic acid of the component (C) is preferably one having 2 to 8 carbon atoms, and specific examples thereof include monocarboxylic acids such as acetic and propionic acids; dicarboxylic acids such as malonic, succinic, glutaric, adipic, maleic, fumaric, and phthalic acids; polycarboxylic acids such as polyglutamic acid; hydroxycarboxylic acids such as glycolic, lactic, hydroxyacrylic, glyceric, malic, tartaric, and citric acids; and acidic amino acids such as glutamic and aspartic acids. Of these acids, hydroxycarboxylic acids having 2 to 6 carbon atoms are preferred, and lactic acid and malic acid are more preferred. Examples of salts of these organic carboxylic acids include salts of the acids with an alkali metal, an alkaline earth metal, ammonia, and an organic amine compound.

Two or more species of the component (C) may be used in combination. The total content thereof in the hair cosmetic composition is preferably from 0.1 to 30% by mass, more preferably from 0.5 to 20% by mass, even more preferably from 0.5 to 10% by mass from the viewpoint of achieving effects of modifying the internal property of hair (such as void repair), an effect of improving hair in stiffness or firmness after the hair is washed, and of improving hair-softness and hair-manageability, and further improving the hair cosmetic composition in setting-performance as a result of the compatibility of the component (C) with the component (A).

The mass ratio of the organic carboxylic acid or the salt thereof as the component (C) to the organic solvent as the component (B) [(C):(B)] is preferably from 10:1 to 1:7, more preferably from 4:1 to 1:3, from the viewpoint of improvement of effects for modifying the internal property of hair (such as void repair), effect for improving stiffness or firmness of hair when the hair is washed, effect for improving hair-softness and hair-manageability, and the like.

When a set polymer of the component (D) is incorporated into the hair cosmetic composition used in the subject invention, the set-retaining ability and a smooth feel of the hair are further improved.

Examples of the set polymer of the component (D) include components 1) to 6) described below. These may be used alone or in combination of two or more thereof.

1) Vinylpyrrolidone Based Polymers:

Polyvinylpyrrolidone; examples of commercially available products thereof include LUVISKOLs K12 and K30 (manufacturedbyBASF), and PVPs K15, and K30 (manufactured by GAF Corp.).

Vinylpyrrolidone/vinyl acetate copolymers; examples of commercially available products thereof include LUVISKOLs VA28, and VA73 (manufactured by BASF SE), and PVP/VAs E-735 and S-630 (manufactured by GAF Corp.).

Vinylpyrrolidone/vinyl acetate/vinyl propionate terpolymer; examples of commercially available products thereof include LUVISKOL VAP343 (manufactured by BASF SE).

Vinylpyrrolidone/alkyl aminoacrylate copolymer; examples of commercially available products thereof include LUVIFLEX (manufactured by BASF SE), and COPOLYMERs 845, 937 and 958 (manufactured by GAF Corp.).

Vinylpyrrolidone/acrylate/(meth)acrylic acid copolymer; examples of commercially available products thereof include LUVIFLEX VBM35 (manufactured by BASF SE).

Vinylpyrrolidone/alkyl aminoacrylate/vinylcaprolactam copolymer; examples of commercially available products thereof include COPOLYMER VC-713 (manufactured by GAF Corp.).

2) Acidic Vinyl Ether Based Polymers:

Methyl vinyl ether/maleic anhydride alkyl-half-ester copolymer; examples of commercially available products thereof include GANTREZ ES-225, ES-425, and SP-215 (manufactured by GAF Corp.).

3) Acidic Polyvinyl Acetate Based Polymers:

Vinyl acetate/crotonic acid copolymer; examples of commercially available products thereof include RESIN 28-1310 (manufactured by National Starch & Chemical Co.), and LUVISET (manufactured by BASF SE).

Vinyl acetate/crotonic acid/vinyl neodecanoate copolymer; examples of commercially available products thereof include RESIN 28-2930 (manufactured by National Starch & Chemical Co.).

Vinyl acetate/crotonic acid/vinyl propionate copolymer; examples of commercially available products thereof include LUVISET CAP (manufactured by BASF SE).

4) Acidic Acrylic Polymers:

(Meth)acrylic acid/(meth)acrylate copolymer; examples of commercially available products thereof include PLUSSIZE (transliterated) L53P (manufactured by Goo Chemical Co., Ltd.), and DIAHOLD (transliterated) (manufactured by Mitsubishi Yuka Co., Ltd.).

Acrylic acid/alkyl acrylate/alkylacrylamide copolymer; examples of commercially available products thereof include ULTRAHOLD 8 (manufactured by BASF SE), and AMPHOMERV-42 (manufactured by National Starch & Chemical Co.).

5) Amphoteric Acrylic Polymers:

(Meth)acrylethylbetaine/alkyl(meth)acrylate copolymer; examples thereof include a copolymer made from N-methacryloyloxyethyl-N,N-dimethylammonium-α-N-methylcarboxybetaine, and an alkyl(meth)acrylate, and examples of commercially available products thereof include YUKA FORMERS M-75, and SM (manufactured by Mitsubishi Yuka Co., Ltd.).

Alkyl acrylate/butylaminoethyl methacrylate/octylacrylamide acrylate copolymer; examples thereof include octylacrylamide/acrylate/butylaminoethyl methacrylate copolymer, and examples of commercially available products thereof include AMPHOMER 28-4910 (manufactured by National Starch & Chemical Co.).

6) Basic Acrylic Polymers:

Acrylamide/acrylic ester copolymer; examples thereof include working examples of JP-A-2-180911 and JP-A-8-291206.

7) Cellulose Derivatives:

Cationic cellulose derivatives; examples of commercially available products thereof include CELQUAT H-100, and L-200 (manufactured by National Starch & Chemical Co.).

8) Chitin or Chitosan Derivative:

Hydroxypropylchitosan; examples of commercially available products thereof include CHITOFILMER (manufactured by Ichimaru Pharcos Co., Ltd.).

Salts each made from carboxymethylchitin, carboxymethylchitosan or chitosan, and a monobasic acid such as pyrrolidone carboxylic, lactic or glycolic acid or the like, or a dibasic acid such as adipic or succinic acid or the like; examples of commercially available products thereof include KYTAMER PC (pyrrolidonecarboxylic acid salt), and KYTAMER L (lactic acid salt) (each manufactured by Union Carbide Corp.).

Of these set polymers, set polymers selected from the group consisting of acrylic polymers, and vinylpyrrolidone based polymers are more preferred. The content of the set polymer is preferably from 0.05 to 20% by mass, more preferably from 0.1 to 10% by mass, even more preferably from 0.3 to 5% by mass of the whole of the hair cosmetic composition.

The hair cosmetic composition used in the subject invention may contain an oily component and a conditioning component selected from silicones other than the organopolysiloxane of the component (A).

The oily component is used to improve the hair-manageability after the hair is dried. Examples of the oily component include hydrocarbons such as squalene, squalane, liquid isoparaffin, light liquid isoparaffin, heavy liquid isoparaffin, α-olefin oligomer, liquid paraffin, and cycloparaffin; glycerides such as castor oil, cacao oil, mink oil, avocado oil, and olive oil; waxes such as beeswax, spermaceti, lanoline, microcrystalline wax, ceresin wax, and carnauba wax; higher alcohols such as cetyl alcohol, oleyl alcohol, stearyl alcohol, isostearyl alcohol, and 2-octyldodecanol; esters such as octyldodecyl myristate, hexyl laurate, cetyl lactate, propylene glycol monostearate, oleyl oleate, hexadecyl 2-ethylhaxanoate, isononyl isononanoate, and tridecyl isononanoate; higher aliphatic acids such as capric acid, lauric acid, myristic acid, palmitic acid, stearic acid, behenic acid, oleic acid, and coconut oil fatty acid, isostearic acid, and isopalmitic acid; solid lipids such as cholesterol, vaseline, cholesteryl isostearate, and sphingolipid; and others oil components such as jojoba oil, isostearyl glyceryl ether, and polyoxypropylene butyl ether. Of these components, squalene, squalane, liquid isoparaffin, light liquid isoparaffin, heavy liquid isoparaffin, α-olefin oligomer, and other branched hydrocarbons are more preferred.

The content of the oil component in the hair cosmetic composition is preferably from 0.05 to 20% by mass, more preferably from 0.1 to 10% by mass, even more preferably from 0.5 to 5% by mass, from the viewpoint of providing preferable hair-manageability, and none-stickiness.

Examples of the silicone include dimethylpolysiloxane, polyether-modified silicone, amino-modified silicone, carboxy-modified silicone, methylphenylpolysiloxane, aliphatic-acid-modified silicone, alcohol-modified silicone, aliphatic-alcohol-modified silicone, epoxy-modified silicone, fluorine-modified silicone, cyclic silicone, and alkyl-modified silicone. Of these silicones, dimethylpolysiloxane, polyether-modified silicone, and amino-modified silicone are preferred.

The dimethylpolysiloxane can provide preferable lubricity to hair. The polyether-modified silicone can provide smoothness to hair. The amino-modified silicone can provide a moist or velvety feel to hair. In the subject invention, various silicones may be used alone or in combination of two or more thereof according to a desired performance. Dimethylpolysiloxane having a viscosities ranging from about 5 mm²/s to about 10,000,000 mm²/s, which is usually supplied in the form of an emulsion, may be used according to a desired feel. Preferred is from 5,000 to 10,000,000 mm²/s, more preferred is 50,000 to 10,000,000 mm²/s.

The polyether-modified silicone may be a silicone having a polyoxyalkylene group. Examples of a group which constitutes the polyoxyalkylene group include an oxyethylene group, and an oxypropylene group. More specific examples of the silicone include KF-6015, KF-945A, KF-6005, KF-6009, KF-6013, KF-6019, KF-6029, KF-6017, KF-6043, KF-353A, KF-354A, and KF-355A (each manufactured by Shin-Etsu Chemical Co., Ltd.); and FZ-2404, SS-2805, FZ-2411, FZ-2412, SH3771M, SH3772M, SH3773M, SH3775M, SH3749, SS-280X series, BY22-008M, BY11-030, and BY25-337 (each manufactured by Dow Corning Toray Co., Ltd.).

The amino-modified silicone is preferably any silicone that has an average molecular weight of about 3,000 to 100,000, and is described in the CTFA dictionary, third edition (Cosmetic Ingredient Dictionary, USA) as any silicone named amodimethicone. Examples of commercially available products thereof include SM 8704C (manufactured by Dow Corning Toray Co., Ltd.); DC 929 (manufactured by Dow Corning Corp.); KT 1989 (manufactured by GE Toshiba Silicones Co., Ltd.); and 8500 Conditioning Agent, DOW CORNING TORAY SS-3588, and DOW CORNING TORAY SILSTYLE 104 (Dow Corning Toray Co., Ltd.).

The content of the silicone in the hair cosmetic composition of the subject invention is preferably from 0.05 to 20% by mass, more preferably from 0.1 to 10% by mass, even more preferably from 0.5 to 5% by mass, from the viewpoint of providing preferable finger-passability through hair and a low hair-stickiness.

The hair cosmetic composition used in the subject invention may contain a surfactant, from the viewpoint of stabilizing the system, which is associated with the solubilization or dispersibility of the solvent, and an improvement in the feel. The surfactant may be cationic surfactant, nonionic surfactant, amphoteric surfactant, and anionic surfactant.

An example of the cationic surfactant is a quaternary ammonium salt represented by the following general formula (9):

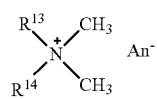

wherein $R^{13}$ and $R^{14}$ are independently a hydrogen atom, an alkyl group having 1 to 28 carbon atoms, or a benzyl group, provided that the $R^{13}$ and $R^{14}$ are not simultaneously a hydrogen atom, a benzyl group, or a lower alkyl group having 1 to 3 carbon atoms, or combination thereof.

One of $R^{13}$ and $R^{14}$ is preferably an alkyl group, more preferably a linear alkyl group having 16 to 24 carbon atoms, even more preferably 22 carbon atoms. The other is preferably a lower alkyl group having 1 to 3 carbon atoms, more a methyl group. Examples of An⁻ include an ethyl sulfate ion, a methyl sulfate ion, a chloride ion, an iodide ion, a sulfate ion, a p-toluenesulfonate ion, and a perchlorate ion.

The cationic surfactant is preferably a long-chain monoalkyl quaternary ammonium salt. Specific examples thereof include cetyltrimethylammonium chloride, stearyltrimethylamonium chloride, alkyltrimethylammonium chloride, behenyltrimethylammonium chloride, and alkylbenzalkonium chloride. Stearyltrimethylammonium chloride, and behenyltrimethylammonium chloride are more preferred.

Examples of the nonionic surfactant include polyoxyalkylene alkyl ether, polyoxyalkylene alkenyl ether, a higher aliphatic acid saccharose ester, polyglycerin aliphatic acid ester, higher aliphatic acid mono- or di-ethanolamide, polyoxyethylene hardened castor oil, polyoxyethylene sorbitan aliphatic acid ester, polyoxyethylene sorbitol aliphatic acid ester, alkyl saccharide surfactant, alkylamineoxide, and alkylamidoamineoxide. Of these surfactants, polyoxyalkylene alkyl ether, and polyoxyethylene hardened castor oil are preferred. Polyoxyethylene alkyl ether, and polyoxyethylene/polyoxypropylene alkyl ether are more preferred.

Examples of the amphoteric surfactant include imidazoline type, carbobetaine type, amidobetaine type, sulfobetaine type, hydroxysulfobetaine type, amidosulfobetaine type surfactants. Of these surfactants, betaine type surfactant such as alkyldimethylaminoacetic acid betaine, aliphatic acid amido propylbetaine, and other betaine type surfactants are preferred. Aliphatic acid amido propylbetaine is more preferred; and this betaine is preferably a betaine having an acyl group having 8 to 18 carbon atoms, more 10 to 16 carbon atoms, and is even more preferably lauric acid amido propylbetaine, palm kernel oil fatty acid amido propylbetaine, and coconut oil fatty acid amido propylbetaine.

Examples of the anionic surfactant include alkylbenzenesulfonates, alkyl or alkenyl ether sulfates, alkyl or alkenyl sulfates, olefinsulfonates, alkanesulfonates, saturated or unsaturated aliphatic acid salts, alkyl or alkenyl ether carbonates, α-sulfonealiphatic acid salts, N-acylamino acid type surfactants, mono- or di-phosphate type surfactants, and sulfosuccinates. About the above-mentioned surfactants, examples of the counter ion to each of their anionic residues include alkali metal ions, such as sodium and potassium ions; alkaline earth metal ions, such as calcium and magnesium ions; an ammonium ion; and alkanolamines having 1 to 3 alkanol groups (each) having 2 or 3 carbon atoms (for example, monoethanolamine, diethanolamine, triethanolamine, and triisopropanolamine). Examples of the counter ion to each of their cationic residues include halide ions, such as a chloride ion, a bromide ion and an iodide ion; a methosulfate ion; and a saccharinate ion.

Of these surfactants, the cationic surfactant and the nonionic surfactant are preferred, from the viewpoint of the feel for touch (of hair treated with the cosmetic composition). The surfactants may be used alone or in combination of two or more thereof. The content thereof in the hair cosmetic composition is preferably from 0.01 to 10% by mass, in more preferably from 0.05 to 5% by mass, from the viewpoint of the stability of the system, which is associated with the solubilization of the solvent, the emulsification of the oily component, and others.

Furthermore, the hair cosmetic composition used in the subject invention may contain a polyhydric alcohol other than the component (B). The polyhydric alcohol contributes to the solubilization of the component (B), and a stable dispersion thereof, and acts synergetically with the component (B) to promote an improvement in hair-sleekness or the effect of modifying hair. The polyhydric alcohol is, for example, ethylene glycol, glycerin, or sorbitol, and is more preferably glycerin. About the polyhydric alcohol, a single species may be used, or two or more thereof may be used in combination.

The content thereof in the hair cosmetic composition is preferably from 0.1 to 10% by mass, more preferably from 0.5 to 5% by mass.

Besides the above-mentioned components, any component that may be used for ordinary hair cosmetic compositions may be incorporated to the hair cosmetic composition used in the subject invention according to the purpose, the usage, and the form (of the hair cosmetic composition), and others. Examples of the component include an antidandruff agent, such as zinc pyrithione, and OCTOPIROX; vitamin agents; bactericides, such as triclosan, and triclocarban; antiinflammatory agents, such as dipotassium glycyrrhizinate, and tocopherol acetate; preservatives, such as methylparaben, and butylparaben; chelating agents; moisturing agents, such as panthenol; coloring agents, such as dyes, and pigments; viscosity adjustors, such as hydroxyethylcellulose, methylcellulose, polyethylene glycol, and clay minerals; pH adjustors, such as organic acids, sodium hydroxide, and potassium hydroxide; vegetable extracts; a pearly sheen agent; perfumes; colorants; ultraviolet absorbents; antioxidants; and other components described in Encyclopedia of Shampoo Ingredients (Micelle Press).

The hair cosmetic composition used in the subject invention can be prepared as various forms in the usual manner. The hair cosmetic composition may be made as, for example, aliquidcomposition for a mist, a lotion, atonic or the like, or a semisolid composition in a gel, paste, creamy or wax form, or the like.

A propellant may be incorporated into the hair cosmetic composition of the subject invention to render the hair cosmetic composition an aerosol type cosmetic composition. The propellant is not particularly limited as far as it is a propellant used ordinarily for hair cosmetic compositions. The propellant may be, for example, a lower saturated hydrocarbon such as propane, butane, or a mixture thereof (examples thereof including a liquefied petroleum gas); an ether such as dimethyl ether; nitrogen gas; carbon dioxide gas; or nitrous oxide gas. These may be used alone or in combination of two or more thereof. The content of the propellant in the hair cosmetic composition of the subject invention is preferably from 0.01 to 50% by mass, more preferably from 5 to 20% by mass.

Furthermore, a composition containing the organopolysiloxane of the component (A) may be filled into a foam discharging container, to prepare the hair cosmetic composition of the subject invention for use in a non-aerosol type hair cosmetic composition. The foam discharging container is not particularly limited as far as the container is a container in which the composition is mixed with the air and the mixture is discharged in the form of foam. Examples thereof include a squeeze foamer, which is used by pressing the main body of soft container with fingers and hands, a pump foamer, which is used by pressing the head of its cap having a pump mechanism with fingers, and a trigger type container.

Examples of the squeeze foamer include foamers described in JP-Y2-62-042785, JP-Y2-62-042786, and JP-Y2-62-042787; and foamers equivalent or similar thereto. Examples of the pump foamer include foamers described in JP-A-7-315463, and JP-A-08-230961; and foamers equivalent or similar thereto. These containers are often equipped with a mesh at the discharging part, in order to improve the quality of foam. Among such containers, a container which is equipped with one or two meshes of 100 to 300 mesh is preferred.

The hair cosmetic composition is preferably used as a hair styling agent, a hair conditioner, or the like. The composition may be prepared preferably as a pump spray, an aerosol spray, a pump foam, or an aerosol foam; or as a gel, a lotion, a mist, a cream, or the like. Of these forms, a form for a pump spray, a pump foam, or an aerosol foam is preferred.

EXAMPLES

Synthesis Example 1

Organopolysiloxane A 6.17 g (0.04 mol) of diethyl sulfate, and 93.8 g (0.947 mol) of 2-ethyl-2-oxazoline were dissolved into 203 g of dehydrated ethyl acetate, and then the solution was refluxed under the $N_2$ atmosphere for 8 hours while heated, thereby synthesizing terminal-reactive poly(N-propionylethyleneimine). The number-average molecular weight thereof was measured by GPC. As a result, the molecular weight was 2500. 33% solution of 100-gram of primary-aminopropyl side-chain-modified polydimethylsiloxane (weight-average molecular weight: 30000, amine equivalent: 2000) in ethyl acetate was added at once. The solution was then refluxed for 10 hours while heated. The reaction mixture was concentrated under reduced pressure to yield an N-propionylethyleneimine/dimethylsiloxane copolymer as a light yellow solid (190 g, yield: 95%). The content of the organopolysiloxane segments in the final product was 50% by mass, and the weight-average molecular weight thereof was 60000. As a result of neutralization titration with hydrochloric acid by use of methanol as a solvent, about 20% by mole of the amino groups were remained.

Synthesis Example 2

Organopolysiloxane B 6.17 g (0.04 mol) of diethyl sulfate, and 106.6 g (1.075 mol) of 2-ethyl-2-oxazoline were dissolved into 229 g of dehydrated ethyl acetate, and then the solution was refluxed under the $N_2$ atmosphere for 8 hours while heated, thereby synthesizing terminal-reactive poly(N-propionylethyleneimine). The number-average molecular weight thereof was measured by GPC. As a result, the molecular weight was 2800. 33% solution of 100-gram of primary-aminopropyl side-chain-modified polydimethylsiloxane (weight-average molecular weight: 30000, amine equivalent: 2000) in ethyl acetate was added at once. The solution was then refluxed for 10 hours while heated. The reaction mixture was concentrated under reduced pressure to yield an N-propionylethyleneimine/dimethylsiloxane copolymer as a light yellow solid (200 g, yield: 94%). The content of the organopolysiloxane segments in the final product was 47% by mass, and the weight-average molecular weight thereof was 64000. As a result of neutralization titration with hydrochloric acid by use of methanol as a solvent, about 20% by mole of the amino groups were remained.

Synthesis Example 3

Organopolysiloxane C 6.17 g (0.04 mol) of diethyl sulfate and 75.7 g (0.763 mol) of 2-ethyl-2-oxazoline were dissolved into 166 g of dehydrated ethyl acetate, and then the solution was refluxed under the $N_2$ atmosphere for 8 hours while heated, thereby synthesizing terminal-reactive poly(N-propionylethyleneimine). The number-average molecular weight thereof was measured by GPC. As a result, the molecular weight was 2000. 33% solution of a 100-gram primary-aminopropyl side-chain-modified polydimethylsiloxane (weight-average molecular weight: 30000, amine equivalent: 2000) in ethyl acetate was added at once. The solution was then refluxed for 10 hours while heated. The reaction mixture was concentrated under reduced pressure to yield an N-propionylethyleneimine/dimethylsiloxane copolymer as a light yellow solid (169 g, yield: 93%). The content of the organopolysiloxane segments in the final product was 55% by mass, and the weight-average molecular weight thereof was 55000. As a result of neutralization titration with hydrochloric acid by use of methanol as a solvent, about 20% by mole of the amino groups were remained.

Synthesis Example 4

Organopolysiloxane D 3.08 g (0.02 mol) of diethyl sulfate, and 96.9 g (0.978 mol) of 2-ethyl-2-oxazoline were dissolved into 203 g of dehydrated ethyl acetate, and then the solution was refluxed under the $N_2$ atmosphere for 8 hours while heated, thereby synthesizing terminal-reactive poly(N-propionylethyleneimine). The number-average molecular weight thereof was measured by GPC. As a result, the molecular weight was 5000. 33% solution of a 100-gram primary-aminopropyl side-chain-modified polydimethylsiloxane (weight-average molecular weight: 40000, amine equivalent: 3800) in ethyl acetate was added at once. The solution was then refluxed for 10 hours while heated. The reaction mixture was concentrated under reduced pressure to yield an N-propionylethyleneimine/dimethylsiloxane copolymer as a light yellow solid (188 g, yield: 94%). The content of the organopolysiloxane segments in the final product was 50% by mass, and the weight-average molecular weight thereof was 80000. As a result of neutralization titration with hydrochloric acid by use of methanol as a solvent, about 24% by mole of the amino groups were remained.

Synthesis Example 5

Organopolysiloxane E 6.17 g (0.04 mol) of diethyl sulfate, and 116.1 g (1.171 mol) of 2-ethyl-2-oxazoline were dissolved into 248 g of dehydrated ethyl acetate, and then the solution was refluxed under the $N_2$ atmosphere for 8 hours while heated, thereby synthesizing terminal-reactive poly(N-propionylethyleneimine). The number-average molecular weight thereof was measured by GPC. As a result, the molecular weight was 3000. 33% solution of a 100-gram primary-aminopropyl side-chain-modified polydimethylsiloxane (weight-average molecular weight: 30000, amine equivalent: 2000) in ethyl acetate was added at once. The solution was then refluxed for 10 hours while heated. The reaction mixture was concentrated under reduced pressure to yield an N-propionylethyleneimine/dimethylsiloxane copolymer as a light yellow solid (204 g, yield: 92%). The content of the organopolysiloxane segments in the final product was 45% by mass, and the weight-average molecular weight thereof was 67000. As a result of neutralization titration with hydrochloric acid by use of methanol as a solvent, about 20% by mole of the amino groups were remained.

Synthesis Example 6

Organopolysiloxane F 6.17 g (0.04 mol) of diethyl sulfate, and 102.2 g (1.031 mol) of 2-ethyl-2-oxazoline were dissolved into 220 g of dehydrated ethyl acetate, and then the solution was refluxed under the N2 atmosphere for 8 hours while heated, thereby synthesizing terminal-reactive poly(N-propionylethyleneimine). The number-average molecular weight thereof was measured by GPC. As a result, the molecular weight was 2700. 33% solution of a 100-gram primary-aminopropyl side-chain-modified polydimethylsiloxane (weight-average molecular weight: 30000, amine equivalent: 2000) in ethyl acetate was added at once. The solution was then refluxed for 10 hours while heated. The reaction mixture was concentrated under reduced pressure to yield an N-propionylethyleneimine/dimethylsiloxane copolymer as a light yellow solid (194 g, yield: 93%). The content of the organopolysiloxane segments in the final product was 48% by mass, and the weight-average molecular weight thereof was 63000. As a result of neutralization titration with hydrochloric acid by use of methanol as a solvent, about 20% by mole of the amino groups were remained.

Synthesis Example 7

Organopolysiloxane G 6.17 g (0.04 mol) of diethyl sulfate, and 86.1 g (0.869 mol) of 2-ethyl-2-oxazoline were dissolved into 187 g of dehydrated ethyl acetate, and then the solution was refluxed under the N2 atmosphere for 8 hours while heated, thereby synthesizing terminal-reactive poly(N-propionylethyleneimine). The number-average molecular weight thereof was measured by GPC. As a result, the molecular weight was 2300. 33% solution of a 100-gram primary-aminopropyl side-chain-modified polydimethylsiloxane (weight-average molecular weight: 30000, amine equivalent: 2000) in ethyl acetate was added at once. The solution was then refluxed for 10 hours while heated. The reaction mixture was concentrated under reduced pressure to yield an N-propionylethyleneimine/dimethylsiloxane copolymer as a light yellow solid (179 g, yield: 93%). The content of the organopolysiloxane segments in the final product was 52% by mass, and the weight-average molecular weight thereof was 58000. As a result of neutralization titration with hydrochloric acid by use of methanol as a solvent, about 20% by mole of the amino groups were remained.

Synthesis Example 8

Organopolysiloxane H 12.78 g (0.0829 mol) of diethyl sulfate, and 246.6 g (2.488 mol) of 2-ethyl-2-oxazoline were dissolved into 519 g of dehydrated ethyl acetate, and then the solution was refluxed under the $N_2$ atmosphere for 15 hours while heated, thereby synthesizing terminal-reactive poly(N-propionylethyleneimine). The number-average molecular weight thereof was measured by GPC. As a result, the molecular weight was 3100. 33% solution of a 166.7-gram primary-aminopropyl side-chain-modified polydimethylsiloxane (weight-average molecular weight: 30000, amine equivalent: 2010) in ethyl acetate was added at once. The solution was then refluxed for 12 hours while heated. The reaction mixture was concentrated under reduced pressure to yield an N-propionylethyleneimine/dimethylsiloxane copolymer as a light yellow solid (422 g, yield: 99%). The content of the organopolysiloxane segments in the final product was 39.4% by mass, and the weight-average molecular weight thereof was 108000. As a result of neutralization titration with hydrochloric acid by use of methanol as a solvent, no amino groups were remained.

Synthesis Example 9

Organopolysiloxane I 5.92 g (0.038 mol) of diethyl sulfate, and 60.7 g (0.613 mol) of 2-ethyl-2-oxazoline were dissolved into 135 g of dehydrated ethyl acetate, and then the solution was refluxed under the $N_2$ atmosphere for 8 hours while heated, thereby synthesizing terminal-reactive poly(N-propionylethyleneimine). The number-average molecular weight thereof was measured by GPC. As a result, the molecular weight was 1700. 33% solution of a 100-gram primary-aminopropyl side-chain-modified polydimethylsiloxane (weight-average molecular weight: 30000, amine equivalent: 1980) in ethyl acetate was added at once. The solution was then refluxed for 10 hours while heated. The reaction mixture was concentrated under reduced pressure to yield an N-propionylethyleneimine/dimethylsiloxane copolymer as a light yellow solid (158 g, yield: 95%). The content of the organopolysiloxane segments in the final product was 60% by mass, and the weight-average molecular weight thereof was 50000. As a result of neutralization titration with hydrochloric acid by use of methanol as a solvent, about 24% by mole of the amino groups were remained.

Synthesis Example 10

Organopolysiloxane J 6.17 g (0.04 mol) of diethyl sulfate, and 50.1 g (0.505 mol) of 2-ethyl-2-oxazoline were dissolved into 114 g of dehydrated ethyl acetate, and then the solution was refluxed under the N2 atmosphere for 8 hours while heated, thereby synthesizing terminal-reactive poly(N-propionylethyleneimine). The number-average molecular weight thereof was measured by GPC. As a result, the molecular weight was 1400. 33% solution of a 100-gram primary-aminopropyl side-chain-modified polydimethylsiloxane (weight-average molecular weight: 32000, amine equivalent: 1900) in ethyl acetate was added at once. The solution was then refluxed for 10 hours while heated. The reaction mixture was concentrated under reduced pressure to yield an N-propionylethyleneimine/dimethylsiloxane copolymer as a light yellow rubbery semisolid (152 g, yield: 97%). The content of the organopolysiloxane segments in the final product was 64% by mass, and the weight-average molecular weight thereof was 50000. As a result of neutralization titration with hydrochloric acid by use of methanol as a solvent, about 24% by mole of the amino groups were remained.

Synthesis Example 11

Organopolysiloxane K 6.17 g (0.04 mol) of diethyl sulfate, and 34.7 g (0.35 mol) of 2-ethyl-2-oxazoline were dissolved into 83 g of dehydrated ethyl acetate, and then the solution was refluxed under the $N_2$ atmosphere for 8 hours while heated, thereby synthesizing terminal-reactive poly(N-propionylethyleneimine). The number-average molecular weight thereof was measured by GPC. As a result, the molecular weight was 1000. 33% solution of a 100-gram primary-aminopropyl side-chain-modified polydimethylsiloxane (weight-average molecular weight: 30000, amine equivalent: 2000) in ethyl acetate was added at once. The solution was then refluxed for 10 hours while heated. The reaction mixture was concentrated under reduced pressure to yield an N-propionylethyleneimine/dimethylsiloxane copolymer as a light yellow rubbery semisolid (141 g, yield: 97%). The content of the organopolysiloxane segments in the final product was 71% by mass, and the weight-average molecular weight thereof was 42000. As a result of neutralization titration with hydrochloric acid by use of methanol as a solvent, about 20% by mole of the amino groups were remained.

Synthesis Example 12

Organopolysiloxane L 0.77 g (0.005 mol) of diethyl sulfate, and 12.9 g (0.13 mol) of 2-ethyl-2-oxazoline were dissolved into 28 g of dehydrated ethyl acetate, and then the solution was refluxed under the $N_2$ atmosphere for 8 hours while heated, thereby synthesizing terminal-reactive poly(N-propionylethyleneimine). The number-average molecular weight thereof was measured by GPC. As a result, the molecular weight was 2700. 33% solution of a 100-gram primary-aminopropyl side-chain-modified polydimethylsiloxane (weight-average molecular weight: 100000, amine equivalent: 20000) in ethyl acetate was added at once. The solution was then refluxed for 10 hours while heated. The reaction mixture was concentrated under reduced pressure to yield an N-propionylethyleneimine/dimethylsiloxane copolymer as a colorless solid (108 g, yield: 95%). The content of the organopolysiloxane segments in the final product was 88% by mass, and the weight-average molecular weight thereof was 114000. As a result of neutralization titration with hydrochloric acid by use of methanol as solvent, no amino group was remained.

Details of the organopolysiloxanes A to L yielded in Synthesis Examples 1 to 12 are collectively shown in Table 1.

Virgin hair tress (Japanese women' hairs not subjected to any chemical treatment, such as hair coloring or bleaching) of 30 cm length and 6 g weight were used for the evaluation.

0.6 g of water was sprayed onto the hair tress, and then 0.2 g of each of the samples was applied to each of several of the tress. The front side of the tress and the rear side thereof were combed 5 times, respectively, with a ring comb manufactured by Delrin Co. Next, the several hair tress were completely dried with a drier, and then five professional panelists were each asked to curl the hair of any one of the tress on an iron (model number: J72010M) manufactured by Kreuz (Co.) and having a temperature set to 150° C., and keep the state for 10 seconds. Thereafter, the panelists were each asked to remove the iron. After the iron was removed, the hair tress was kept in a room-temperature environment, so that the temperature of the hair tress also turned to room temperature before long.

After this successive treatment was finished, functional evaluations and a total evaluation were made according to respective criteria described below. The result of each of these evaluations is the average value of evaluation results made by the five professional panelists.

<Evaluation Criteria>

[Easiness for Waving the Hair Using Hair Iron]

Under the hair tress treatment condition 1, the easiness for curing the hair onto the hair iron was visually evaluated according to the following criteria:
  5: Excellent
  4: Good
  3: Average
  2: Poor
  1: Very Poor

[Finish of the Hair Style]

Under the hair tress treatment condition 1, the degree of waving of the hair tress after the iron was removed was visually evaluated according to the same criteria.

TABLE 1

| Organopolysiloxane | MWox | a/b | MWg | MWsi | MWt | Amine equivalent | Substitution rate |
|---|---|---|---|---|---|---|---|
| A (Synthesis Example 1) | 2,500 | 50/50 | 2,500 | 30,000 | 60,000 | 2,000 | 0.80 |
| B (Synthesis Example 2) | 2,800 | 47/53 | 2,500 | 30,000 | 64,000 | 2,000 | 0.80 |
| C (Synthesis Example 3) | 2,000 | 55/45 | 2,500 | 30,000 | 55,000 | 2,000 | 0.80 |
| D (Synthesis Example 4) | 5,000 | 50/50 | 5,000 | 40,000 | 80,000 | 3,800 | 0.76 |
| E (Synthesis Example 5) | 3,000 | 45/55 | 2,500 | 30,000 | 67,000 | 2,000 | 0.80 |
| F (Synthesis Example 6) | 2,700 | 48/52 | 2,500 | 30,000 | 63,000 | 2,000 | 0.80 |
| G (Synthesis Example 7) | 2,300 | 52/48 | 2,500 | 30,000 | 58,000 | 2,000 | 0.80 |
| H (Synthesis Example 8) | 3,100 | 39.4/60.6 | 2,010 | 30,000 | 108,000 | 2,010 | 1.00 |
| I (Synthesis Example 9) | 1,700 | 60/40 | 2,605 | 30,000 | 50,000 | 1,980 | 0.76 |
| J (Synthesis Example 10) | 1,400 | 64/36 | 2,500 | 32,000 | 50,000 | 1,900 | 0.76 |
| K (Synthesis Example 11) | 1,000 | 71/29 | 2,500 | 30,000 | 42,000 | 2,000 | 0.80 |
| L (Synthesis Example 12) | 2,700 | 88/12 | 20,000 | 100,000 | 114,000 | 20,000 | 1.00 |

$MW_{OX}$: molecular weight of poly(N-acylalkyleneimine) segments,
a/b: mass ratio of the organopolysiloxane segments (a) to the poly(N-acylalkyleneimine) segments (b),
MWg: molecular weight between graft points,
MWsi: molecular weight of the main-chain-constituting organopolysiloxane segments, and
MWt: molecular weight of the organopolysiloxane of the component (A)

Examples 1 to 52, and Comparative Examples 1 to 4

Hair cosmetic compositions shown in Tables 2 to 6 were each prepared, and then evaluated according to methods described below. The results are together shown in the individual tables. About any operation about which no environment is described, the operation was made in an environment having room temperature (25° C.) and a relative humidity of 40%.

Hair Treatment Condition 1 (Treatment for Evaluating the Performance for Waving the Hair by Use of an Iron)

[Feel for Touch (Non-Stiffness)]

Under the hair tress treatment condition 1, the feel for touch (non-stiffness) when the formed portion of the hair was grasped by hand was evaluated by functional evaluation according to the same criteria.

[Style-Retention with Time]

At a temperature of 30° C. and a relative humidity of 800, the hair tress treated according to the hair treatment condition 1 was hung to be left. After the tress being left over 15 minutes, the degree of shape change before and after leaving of the formed portion was visually evaluated (hydrogen bond, which is closely related to retention of hair style, are rapidly loosen when the water content in the air is high; therefore, leaving the hair in an environment of 30° C. temperature and 80% relative humidity for 15 minutes corresponds to leaving the hair in an environment of 25° C. temperature and 40% relative humidity for 12 hours).
- 5: Not changed
- 4: Hardly changed
- 3: Slightly changed
- 2: Changed
- 1: Considerably changed

[Easiness for Re-Waving the Hair]

The hair tress treated according to the treatment condition 1 was re-curled on the iron (model number: J72010M), manufactured by Kreuz, and this state was kept for 10 seconds. According to the following criteria, easiness for re-waving the hair by treatment was visually evaluated:
- 5: Excellent
- 4: Good
- 3: Average
- 2: Poor
- 1: Very Poor

[Total Evaluation]

Total score of easiness for waving the hair using hair iron, finish of the hair style, feel for touch (non-stiffness), hair style retention with time, and easiness for re-waving the hair, using hair iron under the hair Treatment condition 1, was evaluated according to the following criteria:
- 5: Excellent
- 4: Good
- 3: Average
- 2: Poor
- 1: Very Poor

[Set-Retention Against External Force (after Three Times Combing)]

Some of the hair tress waved according to the hair treatment condition 1 were combed three times with a commercially available comb having tooth intervals of 5 mm (manufactured by Y. S. PARK Professional; single-side slender protruding teeth). According to the following criteria, shape change before and after combing of the hair tress was visually evaluated:
- 5: Not changed
- 4: Hardly changed
- 3: Slightly changed
- 2: Changed
- 1: Considerably changed

[Feel for Touch (Bounce and Resilience)]

The hair tress waved according to the hair tress treatment condition 1 was grasped by hand. Feel for touch (bounce and resilience) was functionally evaluated according to the following criteria:
- 5: Bounce and resilience were fully felt,
- 4: Bounce and resilience were fairly felt,
- 3: Difficult to judge whether or not bounce and resilience were felt,
- 2: Bounce and resilience were hardly felt, and
- 1: Bounce and resilience were not felt.

[Hair-Manageability]

Manageability of the hair tress waved according to the hair tress treatment condition 1 was visually evaluated according to the following criteria:
- 5: Fully managed
- 4: Fairly managed
- 3: Average
- 2: Slightly managed
- 1: Not managed

[Feel for Touch (Smoothness)]

The feel for touch (smoothness) of the hair tress waved according to the hair tress treatment condition 1 was functionally evaluated according to the following criteria:
- 5: Excellently smooth
- 4: Smooth
- 3: Average
- 2: Poorly smooth
- 1: No smoothness Hair Treatment Condition 2 (Treatment in the Case of Natural Drying of the Hair Tress without Using Hair Iron)

Hair tress of Caucasian curly hairs (German hairs not treated with any chemical treatment such as hair coloring or bleaching), of 35 cm length and 6 g weight were used for evaluations.

The hair tress was washed with a model shampoo formulated as described below, and redundant water thereon was wiped off with a towel. 0.5 g each of the samples was applied to the wet hair tress. The applied agent was evenly spread using hand and fingers while the hair stream was evenly arranged by the hand and fingers. The tress was naturally dried at room temperature for 3 hours.

After the successive treatment was finished, the hair tress was functionally evaluated according to respective criteria described below. The evaluations were made by five professional panelists. The average of their evaluation results is shown.

| Composition of the model shampoo: | |
|---|---|
| | (% by mass) |
| 25% Sodium polyoxyethylene (2.5) lauryl ether sulfate: | 62.00, |
| diethanol lauric amide: | 2.28, |
| disodium edetate: | 0.10, |
| sodium benzoate: | 0.50, |
| oxybenzone: | 0.03, |
| phosphoric acid (75% aqueous solution): | 0.10, |
| dibutylhydroxytoluene: | 0.01, |
| sodium chloride: | 0.80, |
| Food Red No. 106: | 0.00012, |
| Perfume: | 0.26, and |
| purified water: | balance. |

<Evaluation Criteria>

[Setting-Performance when the Hair Tress was Naturally Dried]

According to the following judging criterion, the degree of arrangement of topology of the curled hair tress treated under the hair tress treatment condition 2 was visually evaluated:
- 5: Hair stream was arranged
- 4: Hair stream was slightly arranged
- 3: Average
- 2: Hair stream was slightly disheveled
- 1: Hair stream was disheveled

[Hair-Style Retaining Performance when the Hair Tress was Naturally Dried]

Hair tress treated under the hair tress treatment condition 2 was left in environment of 30° C. temperature and 80% humidity for 15 minutes. The degree of shape change of the hair tress before and after the leaving was visually evaluated.
- 5: Not changed
- 4: Hardly changed
- 3: Slightly changed
- 2: Changed
- 1: Considerably changed

TABLE 2

| (% by mass) | | Examples | | | | | | | | | | | | | Comparative Examples | | | |
|---|---|---|---|---|---|---|---|---|---|---|---|---|---|---|---|---|---|---|
| | | 1 | 2 | 3 | 4 | 5 | 6 | 7 | 8 | 9 | 10 | 11 | 12 | 13 | 1 | 2 | 3 | 4 |
| Organopolysiloxane A | | 4.0 | 4.0 | 10.0 | 4.0 | 50.0 | | | | | | | | | | | | |
| Organopolysiloxane B | | | | | | | 4.0 | | | | | | | | | | | |
| Organopolysiloxane C | | | | | | | | 4.0 | | | | | | | | | | |
| Organopolysiloxane D | | | | | | | | | 4.0 | | | | | | | | | |
| Organopolysiloxane E | | | | | | | | | | 4.0 | | | | | | | | |
| Organopolysiloxane F | | | | | | | | | | | 4.0 | | | | | | | |
| Organopolysiloxane G | | | | | | | | | | | | 4.0 | | | | | | |
| Organopolysiloxane H | | | | | | | | | | | | | 4.0 | | | | | |
| Organopolysiloxane I | | | | | | | | | | | | | | 4.0 | | | | |
| Organopolysiloxane J | | | | | | | | | | | | | | | 4.0 | | | |
| Organopolysiloxane K | | | | | | | | | | | | | | | | 4.0 | | |
| Organopolysiloxane L | | | | | | | | | | | | | | | | | 4.0 | |
| Ethanol (99.5%) | | | 30.0 | | 96.0 | 50.0 | | | | | | | | | | | | |
| Ion exchange water | | 96.0 | 66.0 | 90.0 | | | 96.0 | 96.0 | 96.0 | 96.0 | 96.0 | 96.0 | 96.0 | 96.0 | 96.0 | 96.0 | 96.0 | 96.0 | 100.0 |
| Evaluations | Easiness for waving the hair using hair iron | 5.0 | 5.0 | 5.0 | 5.0 | 5.0 | 5.0 | 4.4 | 5.0 | 5.0 | 5.0 | 4.8 | 5.0 | 4.0 | 2.4 | 2.0 | 2.0 | 2.0 |
| | Finish of hair style | 5.0 | 5.0 | 5.0 | 5.0 | 5.0 | 4.8 | 4.4 | 5.0 | 5.0 | 5.0 | 4.8 | 5.0 | 4.0 | 2.4 | 2.0 | 2.0 | 2.0 |
| | Feel for touch (non-stiffness) | 5.0 | 5.0 | 5.0 | 5.0 | 5.0 | 4.6 | 5.0 | 4.2 | 4.4 | 4.6 | 5.0 | 4.0 | 5.0 | 3.6 | 5.0 | 5.0 | 5.0 |
| | Hair-style retention with time | 5.0 | 5.0 | 5.0 | 5.0 | 5.0 | 4.8 | 4.2 | 5.0 | 5.0 | 4.8 | 4.2 | 5.0 | 4.0 | 2.4 | 2.0 | 1.0 | 1.0 |
| | Easiness for re-waving the hair | 5.0 | 5.0 | 5.0 | 5.0 | 5.0 | 5.0 | 4.6 | 5.0 | 5.0 | 5.0 | 4.8 | 5.0 | 4.0 | 2.4 | 2.0 | 2.0 | 2.0 |
| | Total evaluation | 5.0 | 5.0 | 5.0 | 5.0 | 5.0 | 4.6 | 4.2 | 4.6 | 4.4 | 4.2 | 4.2 | 3.0 | 3.0 | 1.6 | 1.0 | 1.0 | 1.0 |

TABLE 3

| (% by mass; amounts of components other than component described by concentration are shown as active amount) | | Examples | | | |
|---|---|---|---|---|---|
| | | 14 | 15 | 16 | 17 |
| Organopolysiloxane A | | 4.0 | 3.0 | 5.0 | 5.0 |
| Organopolysiloxane L | | 1.00 | 1.00 | 1.50 | 1.50 |
| Stearyltrimethylammonium chloride (QUARTAMIN-86W, Kao Corp.; 28% by mass) | | 0.85 | 0.85 | 0.85 | 0.85 |
| Polyoxyethylene tridecyl ether (SOFTANOL 90, Nippon Shokubai Co., Ltd.) | | 0.10 | | 0.20 | 0.20 |
| 90% by mass lactic acid | | | | | 1.50 |
| 50% by mass malic acid | | | | | 2.70 |
| Benzyl alcohol | | | | | 0.20 |
| Dipropylene glycol | | | | | 0.50 |
| 48% by mass sodium hydroxide | | | | | Appropriate amount* |
| Polyvinylpyrrolidone (LUVISKOL K-30, BASF SE) | | | | 2.50 | |
| Perfume | | 0.10 | 0.10 | 0.10 | 0.10 |
| Ethanol (99.5%) | | 30.00 | 30.00 | 30.00 | 30.00 |
| Ion exchange water | | Balance | Balance | Balance | Balance |
| Evaluations | Easiness for waving the hair using hair iron | 5.0 | 5.0 | 5.0 | 5.0 |
| | Finish of hair style | 5.0 | 5.0 | 5.0 | 5.0 |
| | Feel for touch (non-stiffness) | 5.0 | 5.0 | 4.0 | 5.0 |
| | Hair-style retention with time | 5.0 | 5.0 | 5.0 | 5.0 |
| | Easiness for re-waving the hair | 5.0 | 5.0 | 5.0 | 5.0 |
| | Total evaluation | 5.0 | 5.0 | 5.0 | 5.0 |

*amount for setting the pH to 3.7

TABLE 4

| (% by mass; shown as active amount) | Examples | | | | | | | | |
|---|---|---|---|---|---|---|---|---|---|
| | 18 | 19 | 20 | 21 | 22 | 23 | 24 | 25 | 26 |
| Organopolysiloxane A | 0.1 | 0.5 | 3.0 | 5.0 | 15.0 | 5.0 | 5.0 | 5.0 | 5.0 |
| Ethanol | | | | | 20.0 | | 10.0 | 20.0 | |
| Benzyl alcohol | | | | | | 0.2 | 1.0 | 5.0 | 0.2 |
| Malic acid | | | | | | 2.0 | 2.0 | 2.0 | 0.5 |
| Vinylpyrrolidone/vinyl acetate copolymer (*) | | | | | | | | | |
| Water | Balance | Balance | Balance | Balance | Balance | Balance | Balance | Balance | Balance |
| Easiness for waving the hair using hair iron | 3.4 | 3.4 | 5.0 | 5.0 | 5.0 | 4.8 | 4.8 | 4.4 | 4.6 |
| Finish of hair style | 3.6 | 3.8 | 5.0 | 5.0 | 5.0 | 4.8 | 4.8 | 4.4 | 4.6 |
| Hair-style retention with time | 3.2 | 3.2 | 5.0 | 5.0 | 5.0 | 4.8 | 5.0 | 4.6 | 4.6 |
| Set-retention against external force | 3.4 | 3.2 | 4.6 | 4.6 | 4.8 | 5.0 | 5.0 | 4.4 | 4.8 |
| Feel for touch (bounce and resilience) | 3.2 | 3.6 | 3.6 | 3.8 | 4.4 | 4.8 | 5.0 | 5.0 | 4.8 |
| Hair-manageability | 3.6 | 3.6 | 3.6 | 3.8 | 4.2 | 4.8 | 5.0 | 5.0 | 4.8 |
| Feel for touch (smoothness) | 3.2 | 3.4 | 3.4 | 3.8 | 3.6 | 4.4 | 4.4 | 4.2 | 4.4 |
| Setting-performance when hair is naturally dried | 3.4 | 3.6 | 4.6 | 4.8 | 4.6 | 4.6 | 4.8 | 4.8 | 4.4 |
| Set-retention when hair is naturally dried | 3.4 | 3.2 | 4.0 | 4.6 | 4.8 | 4.6 | 5.0 | 5.0 | 4.6 |

| (% by mass; shown as active amount) | Examples | | | | | | | | |
|---|---|---|---|---|---|---|---|---|---|
| | 27 | 28 | 29 | 30 | 31 | 32 | 33 | 34 | 35 |
| Organopolysiloxane A | 5.0 | 5.0 | 5.0 | 3.0 | 3.0 | 3.0 | 3.0 | 3.0 | 3.0 |
| Ethanol | 10.0 | 10.0 | 10.0 | | | | | | |
| Benzyl alcohol | 1.0 | 1.0 | 1.0 | | | | | | |
| Malic acid | 0.5 | 1.0 | 5.0 | | | | | | |
| Vinylpyrrolidone/vinyl acetate copolymer (*) | | | | 0.5 | 1.0 | 3.0 | 5.0 | 10.0 | 20.0 |
| Water | Balance | Balance | Balance | Balance | Balance | Balance | Balance | Balance | Balance |
| Easiness for waving the hair using hair iron | 4.6 | 4.4 | 3.8 | 4.4 | 4.6 | 5.0 | 5.0 | 4.4 | 4.2 |
| Finish of hair style | 4.8 | 4.8 | 4.0 | 5.0 | 5.0 | 5.0 | 5.0 | 5.0 | 5.0 |
| Hair-style retention with time | 3.6 | 4.8 | 4.2 | 3.8 | 4.8 | 4.8 | 4.8 | 3.8 | 3.6 |
| Set-retention against external force | 4.8 | 4.8 | 4.4 | 3.8 | 4.4 | 4.8 | 5.0 | 4.4 | 4.0 |
| Feel for touch (bounce and resilience) | 4.8 | 5.0 | 4.8 | 4.0 | 4.8 | 5.0 | 5.0 | 4.8 | 5.0 |
| Hair-manageability | 4.8 | 4.8 | 5.0 | 4.2 | 4.2 | 5.0 | 5.0 | 5.0 | 5.0 |
| Feel for touch (smoothness) | 4.2 | 3.8 | 3.4 | 4.8 | 4.8 | 5.0 | 5.0 | 4.8 | 4.6 |
| Setting-performance when hair is naturally dried | 4.4 | 4.6 | 5.0 | 4.2 | 4.8 | 5.0 | 5.0 | 4.8 | 4.8 |
| Set-retention when hair is naturally dried | 4.2 | 4.6 | 4.8 | 4.0 | 4.6 | 4.6 | 4.8 | 4.8 | 4.8 |

(*): LUVISKOL VA73W, manufactured by BASF SE

TABLE 5

| (% by mass; shown as active amount) | Examples | | | | | | | |
|---|---|---|---|---|---|---|---|---|
| | 36 | 37 | 38 | 39 | 40 | 41 | 42 | 43 |
| Organopolysiloxane A | 5.0 | 5.0 | 5.0 | 5.0 | 5.0 | 5.0 | 5.0 | 5.0 |
| Ethanol | 10.0 | 10.0 | 10.0 | 10.0 | 10.0 | 10.0 | 10.0 | 10.0 |
| Benzyl alcohol | | | 1.0 | | | 1.0 | | |
| Dipropylene glycol | 1.0 | | | 1.0 | | | 1.0 | |
| 1,3-Butanediol | | 1.0 | | | 1.0 | | | 1.0 |
| Malic acid | 2.0 | 2.0 | | | | | | |
| Lactic acid | | | 2.0 | 2.0 | 2.0 | | | |
| Glycolic acid | | | | | | 2.0 | 2.0 | 2.0 |
| Water | Balance | Balance | Balance | Balance | Balance | Balance | Balance | Balance |
| Easiness for waving the hair using hair iron | 4.2 | 3.8 | 4.8 | 4.4 | 4.2 | 4.8 | 4.4 | 4.2 |
| Finish of hair style | 3.8 | 3.6 | 4.6 | 4.0 | 3.8 | 4.8 | 4.0 | 3.8 |
| Hair-style retention with time | 4.2 | 3.6 | 4.8 | 3.8 | 4.2 | 4.8 | 3.8 | 3.8 |

TABLE 5-continued

| (% by mass; shown as active amount) | Examples | | | | | | | |
|---|---|---|---|---|---|---|---|---|
| | 36 | 37 | 38 | 39 | 40 | 41 | 42 | 43 |
| Set-retention against external force | 3.8 | 4.2 | 5.0 | 4.2 | 3.8 | 4.6 | 3.6 | 4.0 |
| Feel for touch (bounce and resilience) | 4.8 | 4.8 | 5.0 | 4.6 | 4.8 | 5.0 | 4.6 | 4.8 |
| Hair-manageability | 4.8 | 4.8 | 5.0 | 4.6 | 4.8 | 5.0 | 4.6 | 4.6 |
| Setting-performance when hair is naturally dried | 4.0 | 4.2 | 4.8 | 4.4 | 4.2 | 4.8 | 3.8 | 4.2 |
| Set-retention when hair is naturally dried | 4.2 | 4.6 | 4.8 | 4.4 | 4.4 | 4.8 | 4.2 | 4.0 |

TABLE 6

| (% by mass; shown as active amount) | Examples | | | | | | | | |
|---|---|---|---|---|---|---|---|---|---|
| | 44 | 45 | 46 | 47 | 48 | 49 | 50 | 51 | 52 |
| Organopolysiloxane A | 3.0 | 3.0 | 3.0 | 3.0 | 3.0 | 3.0 | 3.0 | 3.0 | 3.0 |
| Organopolysiloxane L | | | | | | | 1.5 | 1.5 | 1.5 |
| Polyvinylpyrrolidone (*1) | 3.0 | | | | | | 2.0 | | |
| Vinylpyrrolidone/vinyl acetate copolymer (*2) | | | | | | | | 2.0 | |
| Diethylsulfate (*3) of vinylpyrrolidone/dimethylaminoethyl methacrylate copolymer | | 3.0 | | | | | | | 2.0 |
| Acryaltes/diacetone acrylamide copolymer (*4) | | | 3.0 | | | | | | |
| (Meth)acrylethylbetaine/alkyl (meth)acrylate copolymer (*5) | | | | 3.0 | | | | | |
| Alkylacrylamide/acrylate/alkylaminoalkylacrylamide/polyethylene glycol methacrylate copolymer <mass ratio: 55/20/15/10> (*6) | | | | | 3.0 | | | | |
| t-Butylacrylamide/dimethylacrylamide/dimethylaminopropylacrylamide/methoxypolyethylene glycol (PEG 400) methacrylate copolymer <mass ratio: 52/25/2/21> (*7) | | | | | | 3.0 | | | |
| Water | Balance | Balance | Balance | Balance | Balance | Balance | Balance | Balance | Balance |
| Easiness for waving the hair using hair iron | 5.0 | 5.0 | 5.0 | 5.0 | 4.8 | 4.8 | 5.0 | 5.0 | 5.0 |
| Finish of hair style | 5.0 | 4.8 | 5.0 | 4.8 | 5.0 | 5.0 | 5.0 | 5.0 | 5.0 |
| Hair-style retention with time | 5.0 | 4.8 | 4.8 | 5.0 | 4.8 | 5.0 | 5.0 | 5.0 | 5.0 |
| Hair-style retention against external force | 5.0 | 4.8 | 4.4 | 4.8 | 5.0 | 5.0 | 5.0 | 5.0 | 5.0 |
| Feel for touch (smoothness) | 5.0 | 5.0 | 5.0 | 5.0 | 5.0 | 5.0 | 5.0 | 5.0 | 5.0 |
| Setting-performance when hair is naturally dried | 5.0 | 4.8 | 5.0 | 5.0 | 5.0 | 5.0 | 5.0 | 4.8 | 5.0 |
| Set-retention when hair is naturally dried | 5.0 | 5.0 | 4.8 | 4.8 | 5.0 | 5.0 | 5.0 | 5.0 | 5.0 |

(*1): LUVISKOL K30, manufactured by BASF SE
(*2): LUVISKOL VA73W, manufactured by BASF SE
(*3): GAFQUAT 734, manufactured by ISP (Co.)
(*4): PLAS CIZE L9540B (manufactured by Goo Chemical Co., Ltd.)
(*5): YUKA FORMER M-75, manufactured by Mitsubishi Chemical Corp.
(*6): synthesized according to a method of JP-A-2-180911
(*7): synthesized according to a method of JP-A-8-291206

Examples 53 to 58, and Comparative Examples 5 to 8

Hair cosmetic compositions shown in Table 7 were prepared, and were evaluated after the treatment according to the hair treatment condition 1 which is partially modified. Criteria for the evaluation are as described above. The results are together shown in Table 7.

Example 53

No water was sprayed.

Example 54

The hair tress (used) was not dried with drier.

Example 55

No water was sprayed, and the hair tress was not dried with drier.

Example 56

Sample was applied to the hair at a temperature of 50° C. or higher after heating. The hair was then curled on a hair iron.

Example 57

The hair was curled on a curler instead of hair iron, and then dried using a dryer (the surface temperature of the hair was 80° C.; this condition was also employed in heating with a drier hereinafter). The hair was cooled to room temperature, and the curler was removed.

Example 58

Hair style was formed with a comb while heated with a dryer instead of a hair iron. After the hair style was formed, the comb was removed and the heating with the drier was stopped.

Comparative Example 5

The hair was dried with a drier; however, steps after the treatment with the iron were not conducted.

Comparative Example 6

The hair was dried with a drier, cooled to room temperature, and the hair style was formed with a comb, a brush or the like without heating.

Comparative Example 7

The hair was dried with a drier, cooled to room temperature, and the hair style was formed with a comb, a brush or the like without being heated. Thereafter, the hair was heated to 50° C. or higher.

Comparative Example 8

The hair was dried with a drier, treated with a hair iron in the same way, provided that the hair was heated to 40° C.

TABLE 7

| (% by mass) | | Examples | | | | | | Comparative Examples | | | |
|---|---|---|---|---|---|---|---|---|---|---|---|
| | | 53 | 54 | 55 | 56 | 57 | 58 | 5 | 6 | 7 | 8 |
| Organopolysiloxane A | | 4.0 | 4.0 | 4.0 | 4.0 | 4.0 | 4.0 | 4.0 | 4.0 | 4.0 | 4.0 |
| Ion exchange water | | 96.0 | 96.0 | 96.0 | 96.0 | 96.0 | 96.0 | 96.0 | 96.0 | 96.0 | 96.0 |
| Evaluations | Easiness for waving the hair using hair iron | 5.0 | 5.0 | 5.0 | 5.0 | — | — | — | — | — | 1.0 |
| | Finish of hair style | 5.0 | 5.0 | 5.0 | 5.0 | 5.0 | 5.0 | 1.0 | 1.0 | 1.0 | 1.0 |
| | Feel for touch (non-stiffness) | 5.0 | 5.0 | 5.0 | 5.0 | 5.0 | 5.0 | 5.0 | 5.0 | 5.0 | 5.0 |
| | Hair-style retention with time | 5.0 | 5.0 | 5.0 | 5.0 | 5.0 | 5.0 | 5.0 | 5.0 | 5.0 | 5.0 |
| | Easiness for re-waving the hair | 5.0 | 5.0 | 5.0 | 5.0 | 5.0 | 5.0 | — | — | — | 5.0* |
| | Total evaluation | 5.0 | 5.0 | 5.0 | 5.0 | 5.0 | 5.0 | — | — | — | — |

*The hair was waved at first with the iron at 40° C., and was re-waved at 150° C.

The invention claimed is:

1. A hair styling method comprising:
applying a hair cosmetic composition comprising component (A) to the hair:
Component (A): an organopolysiloxane comprising at least two silicon atoms in an organopolysiloxane segment (a) constituting a main chain of the organopolysiloxane that are each bound to a poly(N-acylalkyleneimine) segment (b) consisting of repeating units represented by general formula (1) via an alkylene group containing a hetero atom:

$$-\!\!+\!\!CH_2\!\!+_n\!\!N\!\!-\!\!\!\!\underset{O}{\overset{\phantom{O}}{\underset{\|}{C}}}\!\!-\!\!R^1 \quad (1)$$

wherein
$R^1$ is a hydrogen atom, an alkyl group having 1 to 22 carbon atoms, an aralkyl group, or an aryl group; and n is 2 or 3;
the number-average molecular weight of each poly(N-acylalkyleneimine) segment (b) is from 1,200 to 5,500,
the mass ratio of the organopolysiloxane segment (a) to the poly(N-acylalkyleneimine) segments (b), (a/b), is from 35/65 to 60/40,
the weight-average molecular weight of each poly(N-acylalkyleneimine) segment (b) is from 1,300 to 5,500, and
the weight-average molecular weight of the organopolysiloxane segment (a) is from 7,000 to 100,000,
wherein:
in component (A) the organopolysiloxane segments (a) and the poly(N-acylalkyleneimine) segments (b) are arranged as set forth in Formula (2), such that the repeating unit is a moiety which is surrounded by a broken line between two points, from a binding point where the poly(N-acylalkyleneimine) segment is bound to the organopolysiloxane segment (binding point α) to a binding point where the adjacent poly(N-acylalkyleneimine) segment is bound to this organopolysiloxane segment (binding point β), which is a segment composed of a single $R^2SiO$ unit, a single $R^6$, and (y+1)-number of $(R^2)_2SiO$ units, and the poly(N-acylalkyleneimine) segments is —W—$R^7$ binding to the $R^6$:

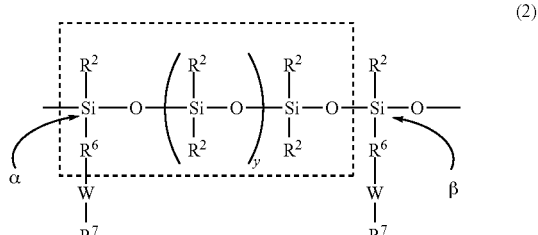

wherein in the Formula (2),
each $R^2$ is independently an alkyl group having 1 to 22 carbon atoms or a phenyl group;
$R^6$ is an alkylene group containing heteroatom;
—W—$R^7$ is a poly(N-acylalkyleneimine) segment;
$R^7$ is a residue of a polymerization initiator; and
y is a positive number;
forming the hair style at a hair temperature of 50° C. or higher;
and subsequently cooling the hair temperature to lower than 50° C. to fix the formed hair style.

2. The hair styling method according to claim 1, wherein at least one silicon atom in the component (A) to which a poly(N-acylalkyleneimine) segment (b) is bounded via the heteroatom-containing alkylene group is a silicon atom other than silicon atoms at both ends of the organopolysiloxane segment (a).

3. The hair styling method according to claim 1, wherein $R^1$ in the general formula (1) is an alkyl group having 1 to 3 carbon atoms.

4. The hair styling method according to claim 1, further comprising cooling the hair prior to, simultaneous with, or after said forming of the hair style, wherein the hair is cooled to a temperature lower than 50° C.

5. The hair styling method according to claim 1, further comprising re-forming the hair style of the hair at a hair temperature of 50° C. or higher, and subsequently cooling the hair temperature to lower than 50° C. to fix the formed hair style.

6. The hair styling method according to claim 1, further comprising applying water to the hair prior to applying the hair cosmetic composition to the hair.

7. The hair styling method according to claim 1, further comprising drying the hair after said applying and before said forming the hair style at a hair temperature of 50° C. or higher.

8. The hair styling method according to claim 4, further comprising re-forming the hair style of the hair at a hair temperature of 50° C. or higher, and subsequently cooling the hair temperature to lower than 50° C. to fix the formed hair style.

9. The hair styling method according to claim 8, further comprising applying water to the hair prior to applying the hair cosmetic composition to the hair.

10. The hair styling method according to claim 9, further comprising drying the hair after said applying and before said forming the hair style at a hair temperature of 50° C. or higher.

\* \* \* \* \*